United States Patent
Robl

(10) Patent No.: US 6,627,636 B2
(45) Date of Patent: Sep. 30, 2003

(54) HMG-COA REDUCTASE INHIBITORS AND METHOD

(75) Inventor: Jeffrey A. Robl, Newtown, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/007,407

(22) Filed: Dec. 4, 2001

(65) Prior Publication Data

US 2002/0094977 A1 Jul. 18, 2002

Related U.S. Application Data

(63) Continuation-in-part of application No. 09/875,155, filed on Jun. 6, 2001, now abandoned.
(60) Provisional application No. 60/211,595, filed on Jun. 15, 2000.

(51) Int. Cl.[7] .............. A61K 31/4353; A61K 31/4365; C07D 491/044; C07D 495/04; A61P 3/06
(52) U.S. Cl. ................. 514/291; 514/292; 514/213.01; 540/577; 546/80; 546/81; 546/89; 546/93
(58) Field of Search .................... 514/291, 292, 514/213.01; 546/80, 81, 89, 93; 540/577

(56) References Cited

U.S. PATENT DOCUMENTS

| | | |
|---|---|---|
| 4,906,624 A | 3/1990 | Chucholowski et al. |
| 4,925,852 A | 5/1990 | Kesseler et al. |
| 5,006,530 A | 4/1991 | Angerbauer et al. |
| 5,169,857 A | 12/1992 | Angerbauer et al. |
| 5,177,080 A | 1/1993 | Angerbauer et al. |
| 5,686,433 A | 11/1997 | Robl |
| 5,753,675 A | 5/1998 | Wattanasin |

FOREIGN PATENT DOCUMENTS

| | | |
|---|---|---|
| EP | 0306929 A2 | 3/1989 |
| EP | 0307342 A2 | 3/1989 |
| EP | 0325129 A2 | 7/1989 |
| EP | 0325130 A2 | 7/1989 |
| EP | 0491226 A | 6/1992 |
| EP | 0444533 A | 9/1997 |
| EP | 0818197 A | 1/1998 |

OTHER PUBLICATIONS

Robl et al, J. Med. Chem., 34, 2804–2815, 1991.

*Primary Examiner*—Evelyn Mei Huang
(74) *Attorney, Agent, or Firm*—Burton Rodney

(57) ABSTRACT

Compounds of the following structure are HMG CoA reductase inhibitors and thus are active in inhibiting cholesterol biosynthesis, modulating blood serum lipids such as lowering LDL cholesterol and/or increasing HDl cholesterol, and treating hyperlipidemia, hypercholesterolemia, hypertriglyceridemia and atherosclerosis

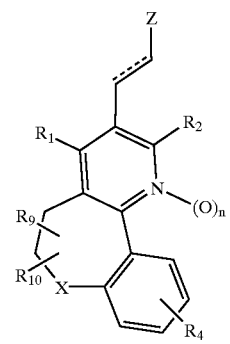

and pharmaceutically acceptable salts thereof, wherein X is O, S, SO, $SO_2$ or $NR_7$; Z is

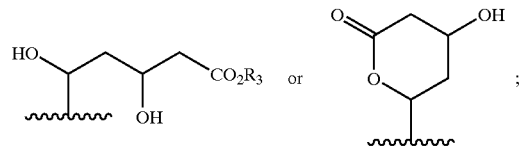

n is 0 or 1; $R_1$ and $R_2$ are the same or different and are independently selected from alkyl, arylalkyl, cycloalkyl, alkenyl, cycloalkenyl, aryl, heteroaryl or cycloheteroalkyl; and $R_3$ to $R_{10}$ are as defined herein.

25 Claims, No Drawings

HMG-COA REDUCTASE INHIBITORS AND METHOD

This application is a continuation-in-part of U.S. application Ser. No. 09/875,155 filed Jun. 6, 2001, abandoned which application claims priority from U.S. provisional application No. 60/211,595, filed Jun. 15, 2000.

FIELD OF THE INVENTION

The present invention relates to compounds and pharmaceutical compositions useful as hypocholesterolemic and hypolipidemic agents. More particularly, this invention concerns (1) certain inhibitors of the enzyme 3-hydroxy-3-methylglutaryl-coenzyme A reductase (HMG-CoA reductase) that include a pyridine containing nucleus attached by means of a linker to an HMG-binding domain sidechain, (2) pharmaceutical compositions containing such compounds and (3) a method of lowering blood serum cholesterol levels and modulating blood serum lipid levels employing such pharmaceutical compositions.

BACKGROUND OF THE INVENTION

U.S. Pat. No. 5,686,433 to Robl discloses the structure

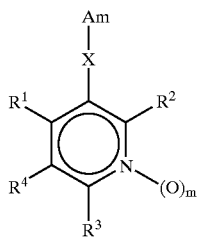

wherein:
Am is a binding domain sidechain;
X is a linker;
$R^1$ and $R^2$ are the same or different and are each independently selected from
(i) hydrogen,
(ii) alkyl,
(iii) aryl,
(iv) cycloalkyl,
(v) aralkyl,
(vi) aralkoxy,
(vii) alkenyl,
(viii) cycloalkenyl, and
(ix) heterocyclo (e.g., thienyl, benzodioxolyl);
$R^3$ is selected from
(i) hydrogen,
(ii) lower alkyl,
(iii) aryl,
(iv) cycloalkyl,
(v) alkoxy,
(vi) aralkyl,
(vii) aralkoxy,
(viii) alkenyl,
(ix) cycloalkenyl,
(x) halo-substituted alkyl,
(xi) adamantyl, and
(xii) heterocyclo (e.g., thienyl, benzodioxolyl);
$R^4$ is selected from
(i) hydrogen,
(ii) lower alkyl,
(iii) aryl,
(iv) cycloalkyl,
(v) alkoxy,
(vi) aralkyl,
(vii) aralkoxy,
(viii) alkenyl,
(ix) cycloalkenyl,
(x) adamantyl,
(xi) halogen,
(xii) halo-substituted alkyl (e.g., trifluoromethyl), and
(xiii) heterocyclo (e.g., thienyl, benzodioxolyl); or $R^3$ and $R^4$ taken together can be

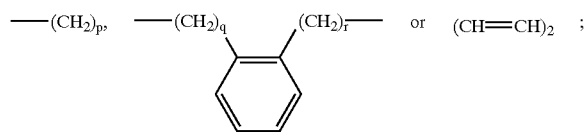

but when $A_m$ is

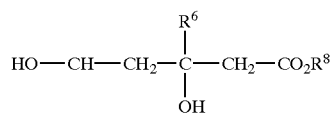

or a δ lactone thereof, $R^3$ and $R^4$ cannot be $(CH=CH)_2$;
$R^6$ is hydrogen or lower alkyl;
$R^8$ is hydrogen, lower alkyl, alkali metal, or alkaline earth metal;
n is 0 or 1;
p is 3, 4 or 5;
q is 0, 1, 2, or 3; and
r is 0, 1, 2, or 3.

In preferred embodiments (Am) is an HMG-binding domain sidechain having a dihydroxy or a phosphinic acid function.

The phosphinic (or phosphonic when X is $CH_2$—O—) acid HMG-binding domain sidechain ($A_1$) is

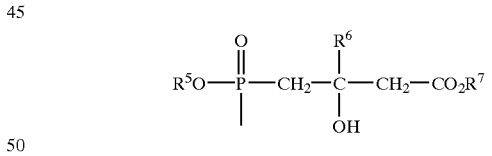

wherein $R^5$ and $R^7$ are independently selected from hydrogen, lower alkyl, alkali metal ion and alkaline earth metal ion; and $R^6$ is hydrogen or lower alkyl.

The dihydroxy acid binding domain sidechain ($A_2$ is

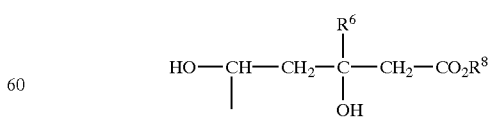

wherein $R^6$ is hydrogen or lower alkyl, $R^8$ is hydrogen or lower alkyl in free acid form or in the form of a physiologically acceptable and hydrolyzable ester or δ lactone thereof (i.e., when Am is

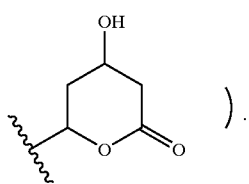

In addition, $R^8$ can be alkali metal ion or alkaline earth metal ion.

A suitable linker (X) is —$(CH_2)_a$—, —CH=CH—, —C≡C—, —$CH_2O$—, wherein O is linked to the phosphorous atom or the aromatic anchor when Am is $A_1$, and wherein O is linked to the aromatic anchor when Am is $A_2$, and wherein "a" is 1, 2, or 3.

BRIEF DESCRIPTION OF THE INVENTION

In accordance with the present invention, there are provided certain pyridine-containing compounds that are potent inhibitors of cholesterol biosynthesis by virtue of their ability to inhibit the enzyme 3-methyl-glutaryl-coenzyme A reductase (HMG-CoA reductase).

In particular, in its broadest chemical compound aspect, the present invention provides compounds of the formula I

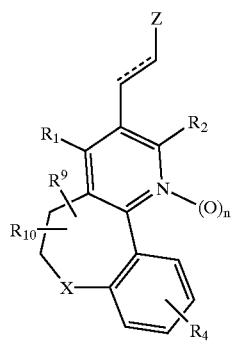

wherein
X is O, S, SO, $SO_2$ or $NR_7$;
Z is

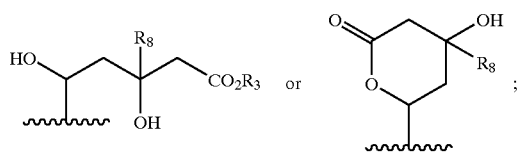

n is 0 or 1;
$R_1$ and $R_2$ are the same or different and are independently selected from alkyl, arylalkyl, cycloalkyl, alkenyl, cycloalkenyl, aryl, heteroaryl or cycloheteroalkyl;
$R_3$ is H, or lower alkyl or a metal ion (such as an alkali metal or an alkaline earth metal);
$R_4$ is H, halogen, $CF_3$, hydroxy, alkyl, alkoxy, carboxyl, carboxylalkyl-, aminoalkyl, amino, alkanoylamino, aroylamino, cyano, alkoxyCON($R_{7d}$)-, $R_{7f}R_{7g}$NCO—, $R_{7f}R_{7g}NCO_2$—, $R_{7e}SO_2N(R_{7d})$-, $R_{7f}R_{7g}NSO_2N(R_{7d})$-, $R_{7e}OCO_2$— or $R_{7e}OCO$—;
$R_7$ is H, alkyl, aryl, alkanoyl, aroyl, alkoxycarbonyl, $R_{7a}SO_2$—, $R_{7b}R_{7c}NSO_2$— or $R_{7b}R_{7c}NCO$—;
$R_{7a}$ and $R_{7e}$ are the same or different and are independently selected from alkyl, arylalkyl, cycloalkyl, alkenyl, cycloalkenyl, aryl, heteroaryl or cycloheteroalkyl,
$R_{7b}$ and $R_{7c}$, and $R_{7f}$ and $R_{7g}$, and $R_{7d}$ are the same or different and are independently selected from H, alkyl, arylalkyl, cycloalkyl, alkenyl, cycloalkenyl, aryl, heteroaryl or cycloheteroalkyl; or $R_{7b}$ and $R_{7c}$ may be taken together with the nitrogen to which they are attached to form a stable 3 to 8 membered heterocyclic ring, which where applicable, includes a total of 1 to 3 heteroatoms in the ring, which heteroatoms may be N, O or S; or $R_{7f}$ and $R_{7g}$ may be taken together with the nitrogen to which they are attached to form a stable 3 to 8 membered heterocyclic ring which, where applicable, includes a total of 1 to 3 heteroatoms in the ring, which heteroatoms may be N, O or S;

$R_8$ is H or lower alkyl;
$R_9$ and $R_{10}$ are the same or different and are independently selected from H or alkyl, or where at least one of $R_9$ and $R_{10}$ is alkyl, $R_9$ and $R_{10}$ may be taken together with the carbon or carbons to which they are attached to form a 3 to 7 membered carbocyclic ring, which may include a spirocyclic ring;

and ⫽ represents a single bond or a double bond (which may be cis or trans);

and including pharmaceutically acceptable salts thereof where $R_3$ is H, esters thereof, prodrug esters thereof, and all stereoisomers thereof.

Preferably, the Z group will be in form of a free acid, a physiologically acceptable and hydrolyzable ester or δ lactone thereof, or an alkali metal salt, alkaline earth metal salt or an amino acid salt.

It is preferred that X is O, $SO_2$ or $NR_7$ where $R_7$ is $R_{7a}SO_2$—.

Preferred are compounds of formula I of the invention wherein
$R_1$ and $R_2$ are independently selected from alkyl, cycloalkyl and aryl;
$R_4$ is H, alkyl or halogen;
X is O; and
n is o.

More preferred are compounds of formula I of the invention wherein $R_1$ is aryl (especially substituted aryl as defined hereinafter);
$R_2$ is alkyl or cycloalkyl;
$R_4$ is H;
$R_9$ and $R_{10}$ are H;
X is O;
n is o; and
⫽ is a double bond.

Still more preferred are compounds of formula I of the invention wherein
$R_1$ is substituted aryl, preferably 4-fluorophenyl, 4-fluoro-3-methylphenyl or 3,5-dimethylphenyl;
$R_2$ is alkyl or cycloalkyl, preferably isopropyl, t-butyl or cyclopropyl;
$R_4$ is H;
X is O;
n is o;
⫽ is a double bond, preferably "trans"; and Z is

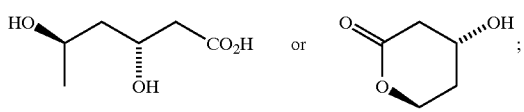

or an alkali or alkaline earth metal salt thereof or an amino acid salt.

Most preferred compounds of formula I of the invention will have the structure

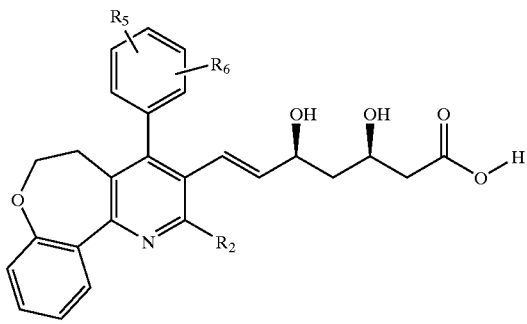

or an alkali or alkaline earth metal (such as Na, K or Ca) salt thereof, or an amino acid salt (such as arginine), wherein $R_5$ and $R_6$ are the same or different and independently selected from H, halogen and/or alkyl (preferably 4-fluoro, 4-fluoro-3-methyl or 3,5-dimethyl); and $R_2$ is alkyl or cycloalkyl, preferably isopropyl, t-butyl or cyclopropyl.

In another aspect, the present invention provides pharmaceutical compositions, useful as hypolipidemic or hypocholesterolemic agents, or hypotriglyceridemic agents, or anti-Alzheimer's agents, or anti-osteoporosis agents as well as other uses as described herein, comprising a hypolipidemic or hypocholesterolemic or hypotriglyceridemic or anti-Alzheimer's disease or anti-osteoporosis amount, or other therapeutically effective amount (depending upon use) of a compound of formula I in accordance with this invention, in combination with a pharmaceutically acceptable carrier.

In another aspect, the present invention provides a method of inhibiting cholesterol biosynthesis or lowering blood serum cholesterol levels and/or modulating blood serum cholesterol levels such as lowering LDL cholesterol and/or increasing HDL cholesterol, or treating dyslipidemia, mixed dyslipidemia, hyperlipidemia, hypercholesterolemia, hypo α-lipoproteinemia, LDL Pattern B, LDL Pattern A, hyperlipoproteinemia or hypertriglyceridemia, and other aberrations of apolipoprotein B metabolism, or reducing levels of Lp(a), or treating or preventing other cholesterol-related diseases, or treating or preventing or reversing progression of atherosclerosis, or preventing or treating Alzheimer's disease, or preventing or treating osteoporosis and/or osteopenia, or reducing inflammatory markers such as C-reactive protein, or preventing or treating low grade vascular inflammation, or preventing or treating stroke, or preventing or treating dementia, or preventing and treating coronary heart disease (including primary and secondary prevention of myocardial infarction), or preventing or treating stable and unstable angina, or primary prevention of coronary events, or secondary prevention of cardiovascular events, or preventing or treating peripheral vascular disease, preventing or treating peripheral arterial disease, or preventing or treating acute vascular syndromes, or preventing or reducing the risk of undergoing myocardial revascularization procedures, or preventing or treating microvascular diseases such as nephropathy, neuropathy, retinopathy and nephrotic syndrome or preventing or treating hypertension in a patient in need of such treatment by administering a pharmaceutical composition in accordance with the present invention as defined above.

In addition, in accordance with the present invention, a method is provided for preventing or treating diabetes, especially Type 2 diabetes, and related diseases such as insulin resistance, hyperglycemia, hyperinsulinemia, elevated blood levels of fatty acids or glycerol, obesity, Syndrome X, diabetic complications, dysmetabolic syndrome, and related diseases, and sexual dysfunction, wherein a therapeutically effective amount of a compound of structure I is administered to a patient in need of treatment.

In addition, in accordance with the present invention, a method is provided for preventing and treating malignant lesions (such as ductal carcinoma in situ of the breast and lobular carcinoma in situ of the breast), premalignant lesions (such as fibroadenoma of the breast and prostatic intraepithelial neoplasia (PIN), gastrointestinal malignencies, liposarcomas and various other epithelial tumors (including breast, prostate, colon, ovarian, gastric and lung), cancer-induced asthenia (fatigue), irritable bowel syndrome, Crohn's disease, gastric ulceritis, and gallstones, and HIV infection, other infectious diseases, drug-induced lipodystrophy, and proliferative diseases such as psoriasis, wherein a therapeutically effective amount of a compound of structure I is administered to a human patient in need of treatment.

In addition, in accordance with the present invention, a method is provided for improving coagulation homeostasis including reducing PAI-1 activity, reducing fibrinogen, and/or reducing platelet aggregation, and/or improving endothelial function, wherein a therapeutically effective amount of a compound of structure I is administered to a patient in need of treatment.

In addition, in accordance with the present invention, a method is provided for treating cholesterol related diseases, diabetes and related diseases, cardiovascular diseases, cerebrovascular diseases as defined above and hereinafter and other diseases as set out above, wherein a therapeutically effective amount of a combination of a compound of structure I and a hypolipidemic agent, and/or lipid modulating agent and/or antidiabetic agent and/or cardiovascular agent, cerebrovascular agent, and/or other type of therapeutic agent, is administered to a patient in need of treatment.

In the above methods of the invention wherein a combination is administered, the compound of structure I will be employed in a weight ratio to the other therapeutic agent (depending upon its mode of operation) within the range from about 0.01:1 to about 500:1, preferably from about 0.5:1 to about 100:1.

DETAILED DESCRIPTION OF THE INVENTION

In accordance with the present invention, there is provided compounds useful in inhibiting the enzyme HMG-CoA reductase, which inhibitors are useful as hypocholesterolemic agents, dyslipidemic agents, hypolipidemic agents, hypotriglyceridemic agents, anti-Alzheimer's disease agents, and antiosteoporosis agents as well as other uses as described herein.

The term "coronary events" as employed herein refers to myocardial infarction, myocardial revascularization procedures, angina, cardiovascular death and acute coronary syndrome.

The term "cardiovascular diseases or events" as employed herein refers to atherosclerosis of the coronary arteries, myocardial infarction, including primary MI and secondary MI, recurrent myocardial infarction, angina pectoris (including stable and unstable angina), congestive heart failure, and sudden cardiac death.

The term "cerebrovascular diseases or events" as employed herein refers to cerebral infarction or stroke (caused by vessel blockage or hemmorage), or transient ischemia attack (TIA), syncope, atherosclerosis of the intracranial and/or extracranial arteries, and the like.

The term "cholesterol-related diseases" as employed herein refers to diseases involving elevated levels of LDL cholesterol, diseases involving regulation of LDL receptors, diseases involving reduced levels of HDL cholesterol, dyslipidemia, hyperlipidemia, elevated LDL Pattern B, elevated LDL Pattern A, hypercholesterolemia, hypo α-lipoproteinemia (low HDL cholesterol syndrome), hyperlipoproteinemia, elevated Lp(a) levels, hypertriglyceridemia, other aberrations of apolipoprotein B metabolism, heterozygous familial, presumed familial combined and non-familial (non-FH) forms of primary hypercholesterolemia (including Frederickson Types IIa and IIb), cholesterol ester storage disease, and cholesterol ester transfer protein disease, and related diseases.

The conditions, diseases, and maladies collectively referenced to as "Syndrome X" or Dysmetabolic Syndrome (as detailed in Johanson, *J. Clin. Endocrinol. Metab.*, 1997, 82, 727–734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), other types of anti-atherosclerosis agents, and/or one or more antiplatelet agents, one or more agents for treating hypertension, one or more anti-cancer drugs, one or more agents for treating arthritis, one or more anti-osteoporosis agents, one or more anti-obesity agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

The term "other types of anti-atherosclerosis agents" as employed herein refers to conventional anti-atherosclerosis agents including lipoxygenase inhibitors, ACAT inhibitors, antioxidants, PPAR δ agonists, phospholipase inhibitors including PLA-2 inhibitors and/or other known anti-atherosclerotic agents.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1–C4) alkyl or arylsulfonic acids which are unsubstituted or substituted, for example by halogen, for example methanesulfonic acid or p-toluenesulfonic acid.

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, cycloheteroalkyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

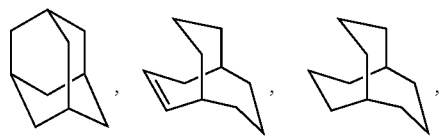

-continued

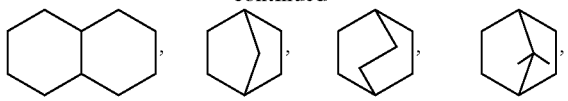

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, heteroaryl, cycloheteroalkyl, amino, alkylamino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted with 1 or 2 substituents as defined above for "alkyl", such as, for example, alkyl, halo, hydroxy, alkoxy and/or cycloalkyl.

Where alkenyl groups as defined above and alkynyl groups as defined above, respectively, have single bonds for attachment at two different carbon atoms, they are termed "alkenylene groups" and "alkynylene groups", respectively, and may optionally be substituted with 1 or 2 substituents as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

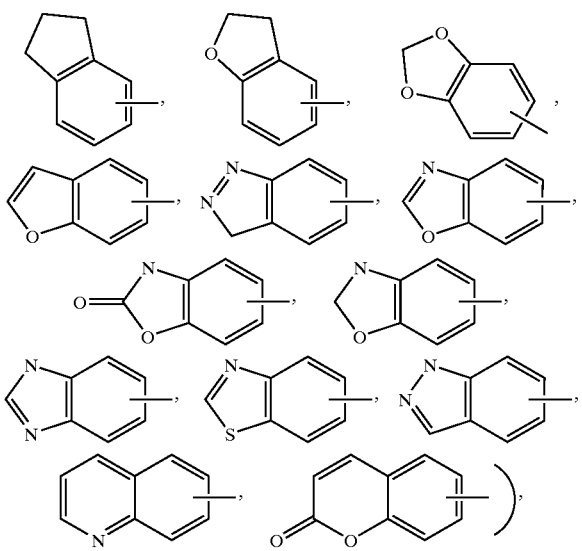

and may be optionally substituted through available carbon atoms with 1, 2, or 3 groups selected from hydrogen, halo, haloalkyl, alkyl, haloalkyl, alkoxy, halophenyl, benzoyloxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, alkanoyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as

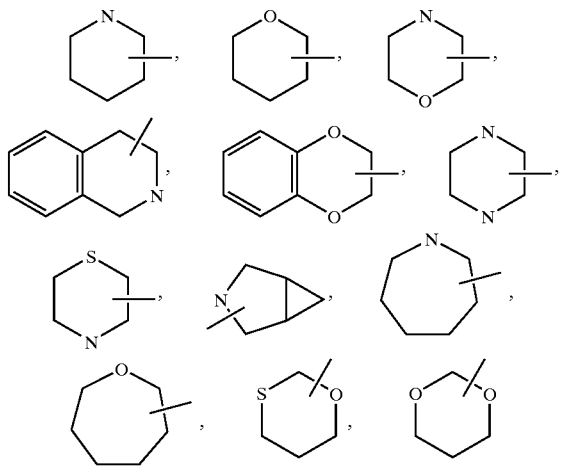

and the like. The above groups may include 1 to 4 substituents such as alkyl, halo, oxo and/or any of of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

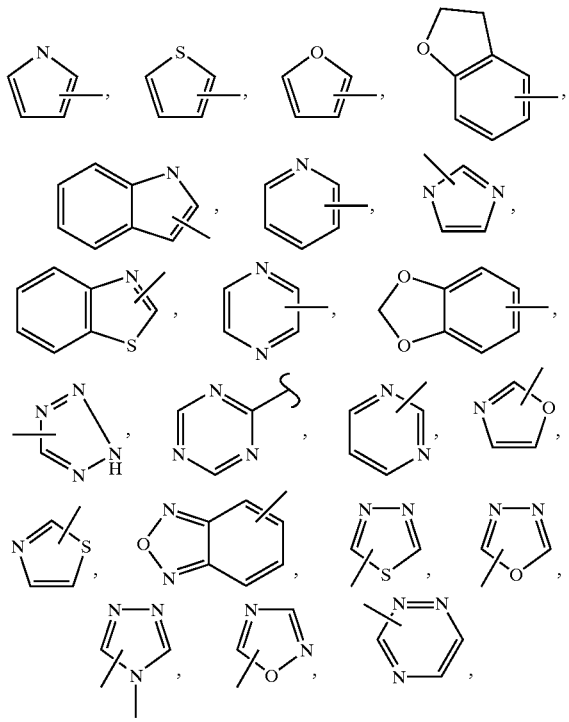

and the like.

The term "cycloheteroalkylalkyl" as used herein alone or as part of another gorup refers to cycloheteroalkyl groups as defined above linked through a C atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a —$(CH_2)_r$-chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkoxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. In addition, prodrug esters which are known in the art for carboxylic and phosphorus acid esters such as methyl, ethyl, benzyl and the like.

Examples of such prodrug esters include

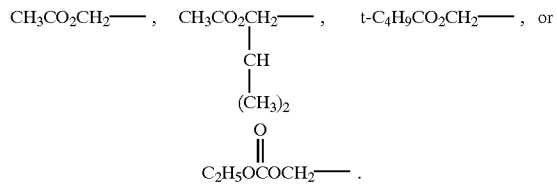

Other examples of suitable prodrug esters include

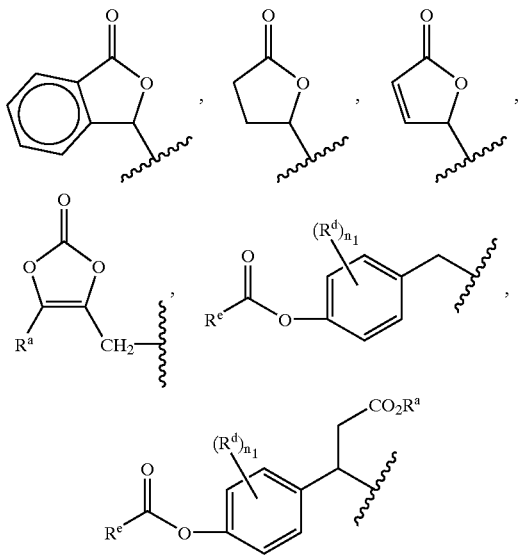

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

Compounds of the invention may be prepared by the following method.

Referring to Reaction Scheme 1, Knovenagel condensation of readily available beta-keto ester 1, where R is lower alkyl, with aldehyde 2 under standard conditions (e.g. HOAc, piperidine, toluene, reflux) affords the corresponding adduct 3. Base induced 1,4-addition of ketone 4 (e.g. LiN(TMS)$_2$ in THF or EtONa in EtOH) provides the adduct 5, usually as a mixture of diastereomers.

Conversion of the 1,5-diketone 5 to the pyridyl ester 6 may be effected by treatment with an ammonia source (such as NH$_4$OAc) in the presence of an oxidant (such as Cu(OAc)2 or oxygen) in a suitable solvent (such as refluxing HOAc), or by reaction of 5 with hydroxylamine hydrochloride in HOAc with heat. The ester functionality of 6 can be reduced by standard methods (LiAlH$_4$, DIBAL, LiBH$_4$) to give alcohol 7 which can subsequently be converted to the corresponding halide 8 (e.g. PBr$_3$ in CH$_2$Cl$_2$, CBr$_4$/PPh$_3$ in CH$_3$CN or POCl$_3$). Conversion of halide 8 to the phosphorus compound 9 where W is Ph or alkyl is effected by treatment of 8 with W$_2$POEt in toluene. Conversion of halide 8 to compound 9 where W is OR (R is lower alkyl) may be effected by the reaction of 8 with HOP(OR)2/base/THF or by Arbuzov reaction with P(OR)$_3$.

In the case where X is S in Scheme 1, the sulfide may be converted to either the sulfoxide (X=SO) or sulfone (X=SO$_2$) at multitude points in the synthesis. Thus, compounds 4, 5, 6, 7, 8, or 9 where X is S may be converted to the desired sulfoxides or sulfones via standard methods of oxidation (m-CPBA, CH$_2$Cl$_2$; aq H$_2$O$_2$, conc. HCl, Na$_2$WO$_4$, toluene or alcoholic solvent; aq H$_2$O$_2$, MeReO$_3$, alcoholic solvent; excess HOF, CH$_3$CN, CHCl$_3$; N-methylmorpholine N-oxide, OsO$_4$, acetone, H$_2$O; aq H$_2$O$_2$, SeO$_2$, aq HCl; H$_2$O$_2$, HOAc, HCl; H$_2$O$_2$, ammonium paramolybdate, HClO$_4$, HOAc).

In the case where X is NR$_7$, R$_7$ may be R$_{7a}$SO$_2$—, R$_{7b}$R$_{7c}$NSO$_2$-or R$_{7b}$R$_{7c}$NCO— starting with intermediate 4 for conversion to the final product Ia or Ib. Alternately, one may utilize intermediate 4 where X is NR$_7$ and R$_7$ is a suitable nitrogen protecting group (e.g. Boc, Cbz, TFA, FMOC, alloc, trityl, benzhydryl) and execute the reaction scheme through intermediates 5, 6, 7, 8, 9 or 11. At these intermediate steps the nitrogen protecting group may be removed to generate the free NH functionality which can subsequently be reacted with O=C=NR$_{7b}$, R$_{7a}$SO$_2$Cl or NR$_{7b}$R$_{7c}$SO$_2$Cl, or, via a two step procedure be reacted with SOCl$_2$ or COCl$_2$ followed by R$_{7a}$OH or HNR$_{7b}$R$_{7c}$ to afford the desired adducts.

Witting reaction between 9 and aldehyde 10 (aldehyde 10 has been previously described in U.S. Pat. No. 5,686,433) may be effected under standard conditions with base (n-BuLi, LiN(TMS)$_2$, LDA) in an appropriate solvent (THF, Et$_2$O, toluene, DMPU) to afford the adduct 11. Treatment of 11 under acidic conditions (e.g. TFA, HCl) effects the conversion of 11 to lactone Ia. Saponification of Ia to Ib (where R$_3$ is alkali metal, or alkaline earth metal) can be effected by treatment of Ia with aqueous base or subsequently acidified to give Ib where R$_3$ is H. Additionally, Ia can be treated with an alcohol of the type R$_3$OH under basic conditions to form the corresponding esters of Ib.

As seen in Reaction Scheme 2, the saturated derivatives of compound I (where ⫽ is CH$_2$—CH$_2$) are obtained by catalytic (Pd/C, Pt/C, Pd(OH)$_2$) hydrogenation of 11, Ia, or Ib to afford 12, Ic, or Id, respectively. Compound 12 may be converted to Ic and Id following the earlier described methods for the conversion of compound 11 to Ia and Ib.

Scheme 1
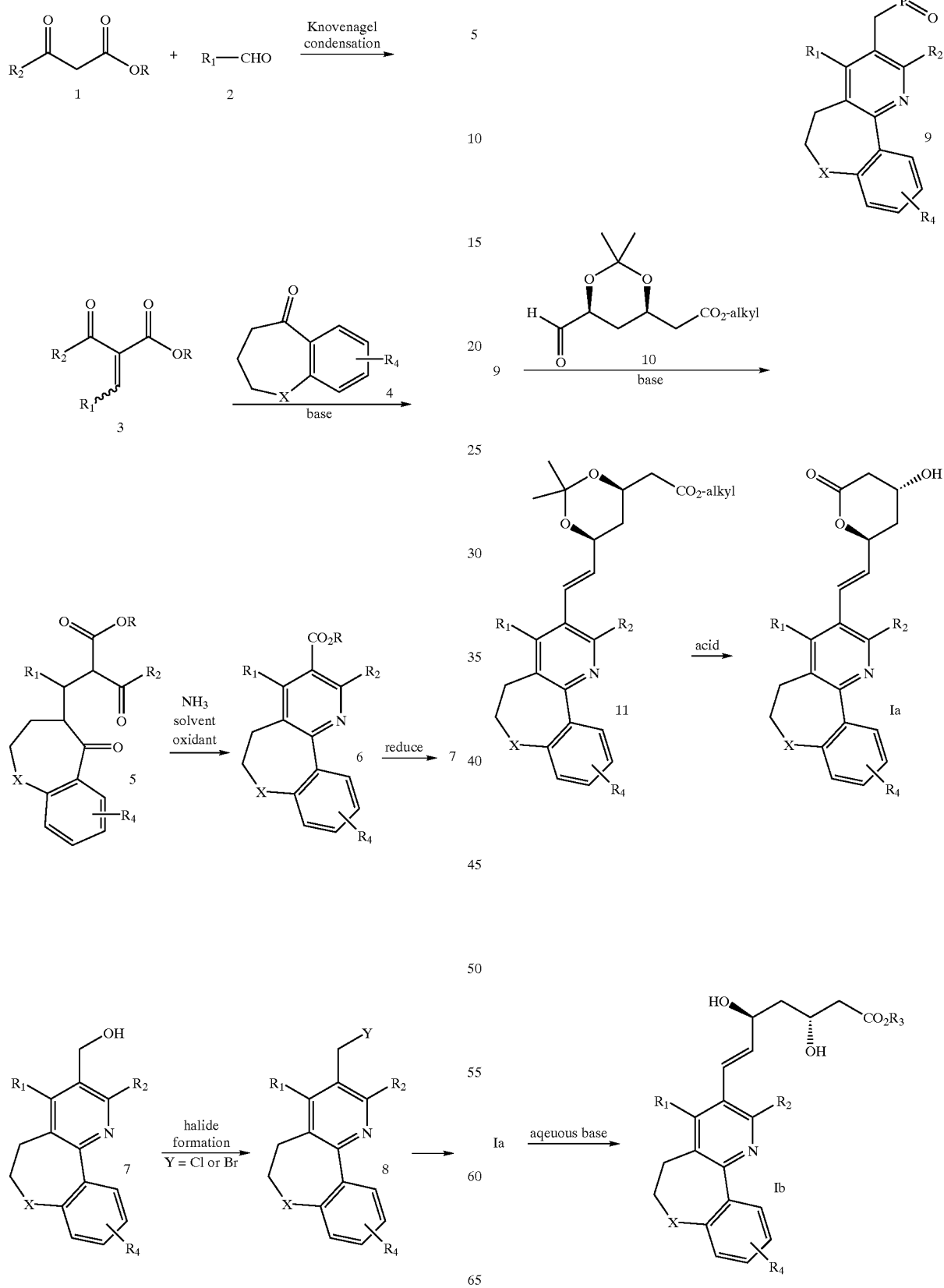

Scheme 2

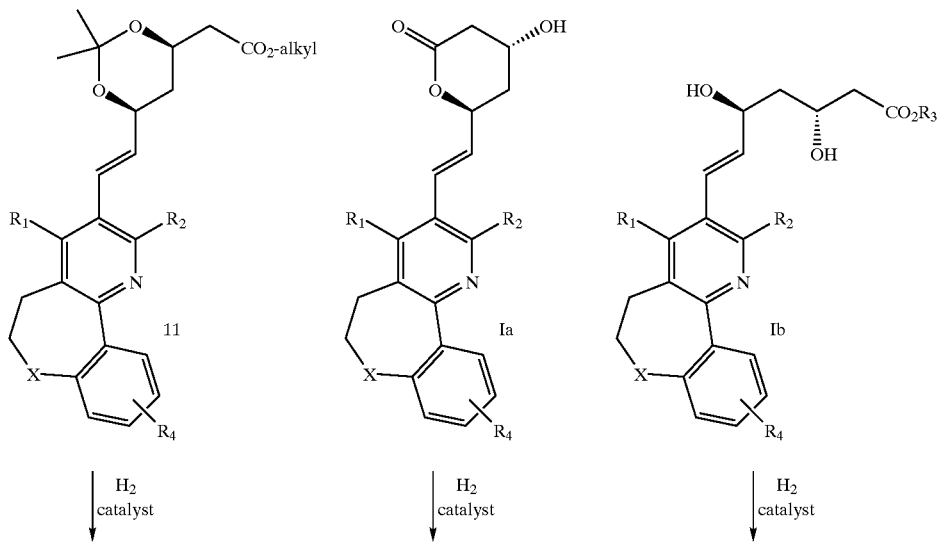

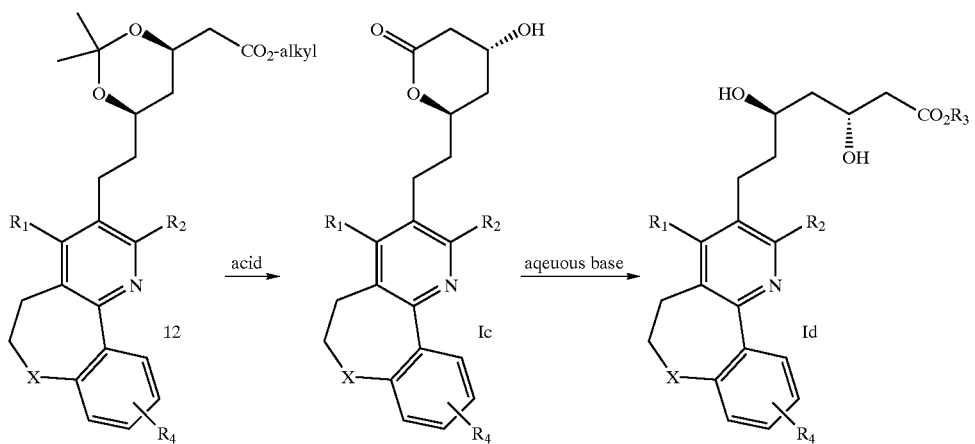

The synthesis of compounds I wherein ⫽ is CH=CH and n is 1, is described in Scheme 3. Bis-silylation of compound $Ib^1$ with a bulky silylchloride (e.g., ClSi(t-butyl)Ph$_2$, ClSi(t-butyl)Me$_2$, ClSiPh$_3$) in the presence of a suitable base (e.g., TEA, imidazole, pyridine) and solvent (e.g., CH$_2$Cl$_2$, THF) provides compound $Ib^2$. Treatment of $Ib^2$ with oxidants such as m-CPBA or CF$_3$CO$_3$H 10 in an appropriate solvent such as CH$_2$Cl$_2$ or HOAc affords N-oxide $Ib^3$. Desilylation of $Ib^3$ (TBAF/HOAc/THF or HF/CH$_3$CN) gives $Ib^4$ which may be saponified to $Ib^5$ using aqueous solutions of a metal hydroxide in an appropriate solvent (e.g., MeOH, dioxane).

SCHEME 3

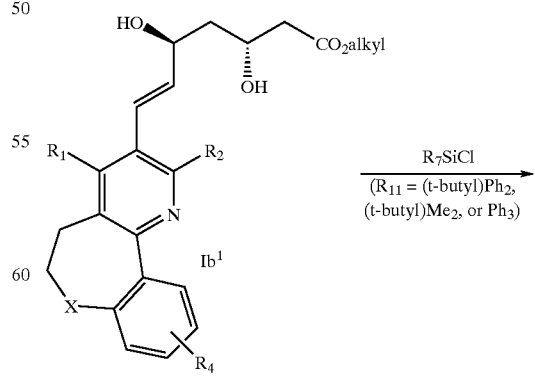

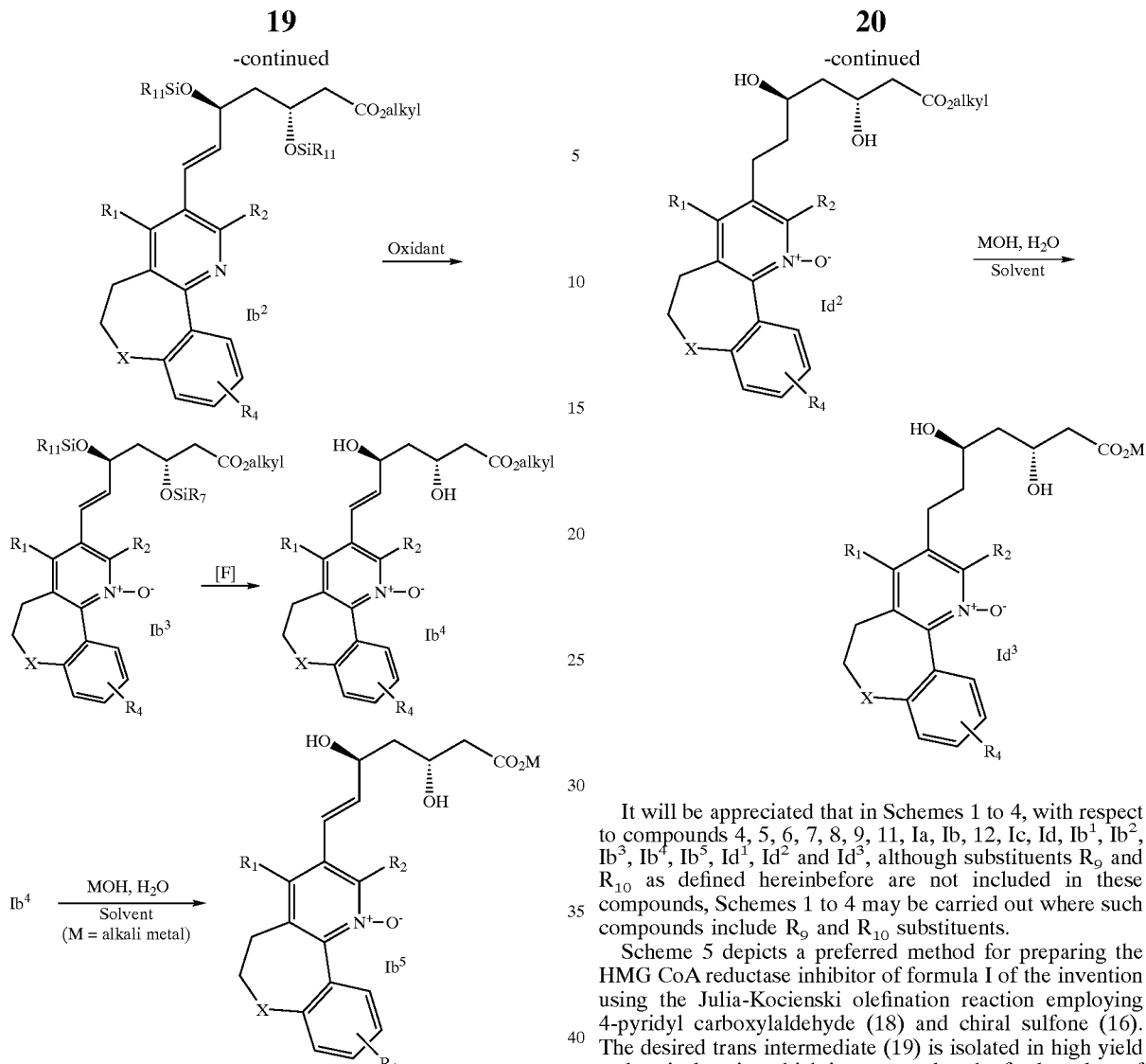

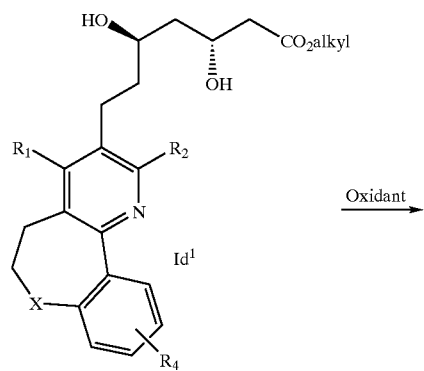

Additionally, compound Id$^1$ may be oxidized and saponified, as described above, to provide compounds I wherein ⟆ is CH$_2$CH$_2$ and n is 1 (e.g., compounds Id$^2$ and ID$^3$) as shown in Scheme 4.

SCHEME 4

It will be appreciated that in Schemes 1 to 4, with respect to compounds 4, 5, 6, 7, 8, 9, 11, Ia, Ib, 12, Ic, Id, Ib$^1$, Ib$^2$, Ib$^3$, Ib$^4$, Ib$^5$, Id$^1$, Id$^2$ and Id$^3$, although substituents R$_9$ and R$_{10}$ as defined hereinbefore are not included in these compounds, Schemes 1 to 4 may be carried out where such compounds include R$_9$ and R$_{10}$ substituents.

Scheme 5 depicts a preferred method for preparing the HMG CoA reductase inhibitor of formula I of the invention using the Julia-Kocienski olefination reaction employing 4-pyridyl carboxylaldehyde (18) and chiral sulfone (16). The desired trans intermediate (19) is isolated in high yield and optical purity which is converted to the final product of the invention. As will be seen, the chiral sulfone (16), a key intermediate in the Julia-Kocienski step, is prepared in three steps starting from the commercially available Kaneka alcohol (12) via triflate (13) and sulfide intermediate (15).

Referring to Scheme 5, treatment of commercially available chiral alcohol (12) with triflic anhydride and triethylamine in dichloromethane at low temperature (for example 0 to –30° C.) affords triflate (13). Other pyridine or amine bases may be employed. Triflate (13) (without being isolated) is carried onto the next step without further purification. A methylene chloride solution of triflate (13) is treated with 1-phenyl-1H-tetrazole-5-thiol (14) to provide the chiral sulfide (15) which is oxidized with hydrogen peroxide in the presence of catalytic ammonium heptamolybdate tetrahydrate to give crystalline sulfone (16). Other oxidant, such as m-chloro-p-benzoic acid (mCPBA) mey be employed.

Addition of LiHMDS or NaHMDS to a mixture of sulfone (16) and pyridine carboxylaldehyde (18) in THF at low temperature (–78 to –35° C.) provides trans olefin (19) in high diastereoselectivity (>99%).

The pyridine aldehyde (18) is obtained as a crystalline solid form the corresponding ester (17). Reduction of ester (17) with Red-Al followed by oxidation with Tempo (2,2, 6,6-tetramethyl-1-piperidinyloxy) gives aldehyde (18) in high yield. The final compound Ie of the invention is prepared in a one pot procedure starting from (19) without isolating any intermediates. Removal of acetonide under acidic condition provides diol Ie of the invention which upon further treatment with sodium hydroxide gives the sodium salt of the acid If of the invention. Subsequent treatment of If with acid followed by the addition of arginine produces crystalline arginine salt of the invention Ig.
Scheme 5
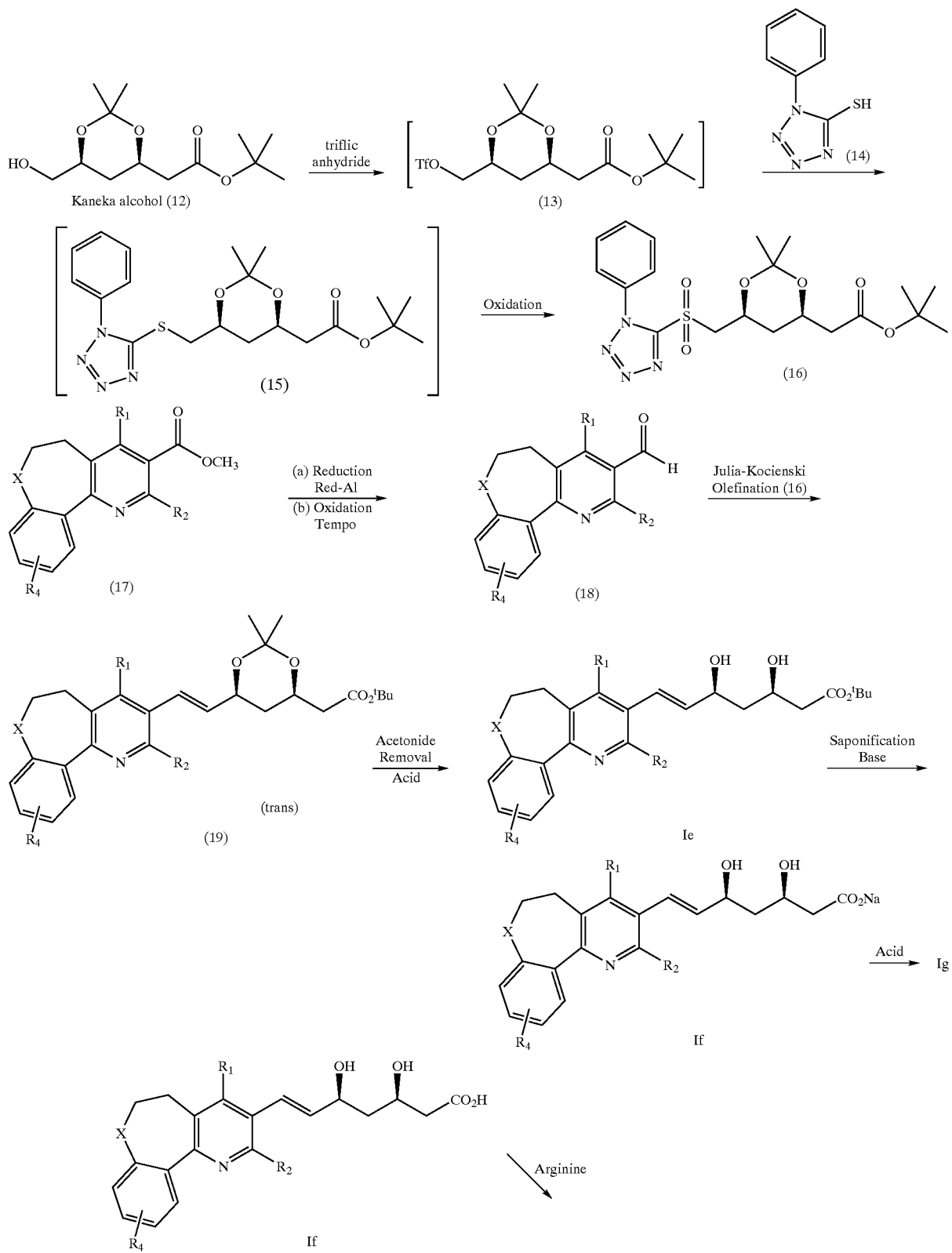

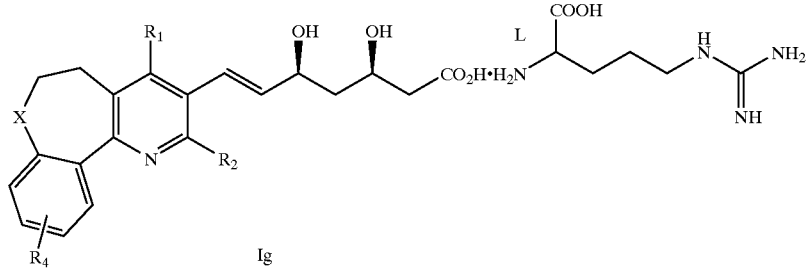

Ig

In addition, in accordance with the present invention, intermediates 6, 7, 8, 9, 11 and 12 are novel compounds and form part of the present invention. These compounds have the general structure II

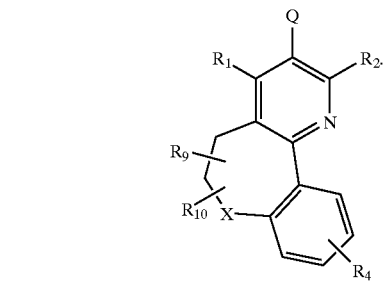

wherein X is O, S, SO, $SO_2$ or $NR_7$, $R_1$, $R_2$, $R_4$, $R_7$, $R_9$ and $R_{10}$ as are as defined above, Q is

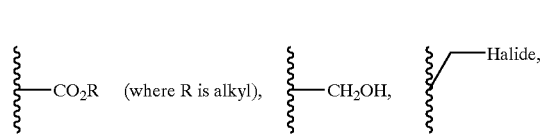

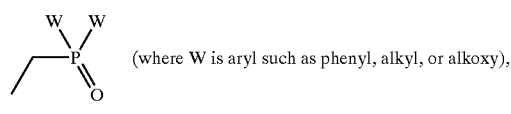

(where W is aryl such as phenyl, alkyl, or alkoxy), or

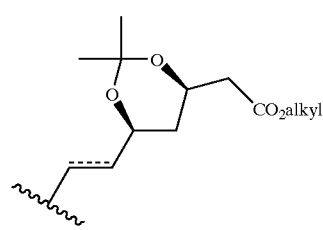

Thus, the intermediates of the invention can have the following structures:

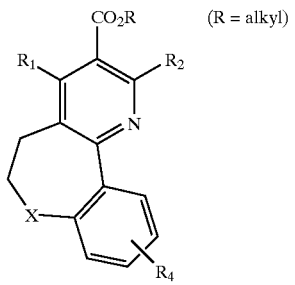

6

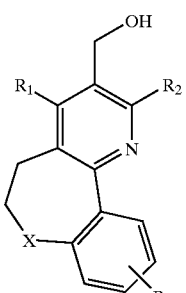

7

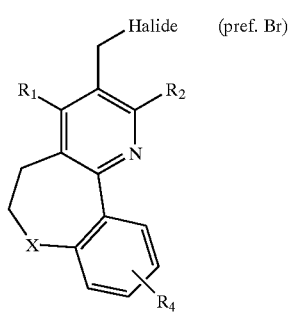

8

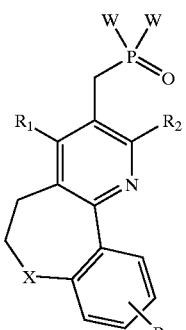

9

(W = aryl or alkoxy)

-continued

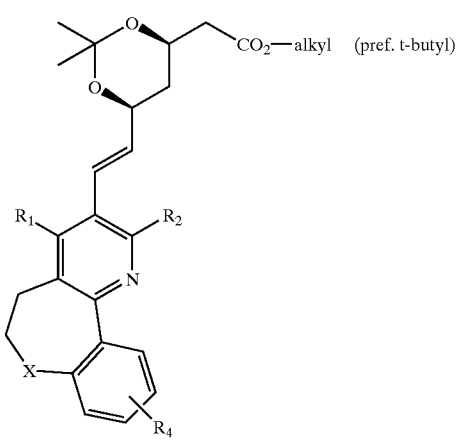
11

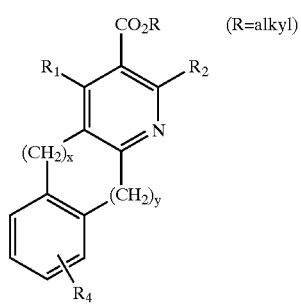
12

Compounds 6, 7, 8, 9, 11 and/or 12 may include $R_9$ and $R_{10}$ substituents.

Compounds containing dihydroxy acid HMG-CoA binding domain side chains may be prepared in homochiral form, which is preferred, or may be prepared as racemic mixtures (3S*, 5R*) and may later be resolved to obtain the 3S, 5R isomer.

Thus, the intermediates of the invention can have the following structures:

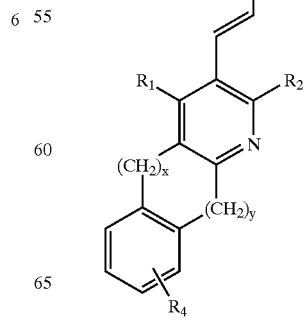
6

-continued

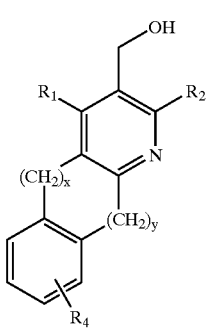
7

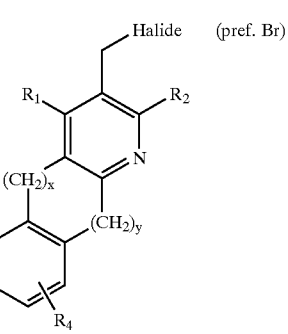
8

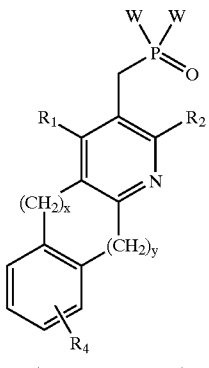
9

(W = aryl or alkoxy)

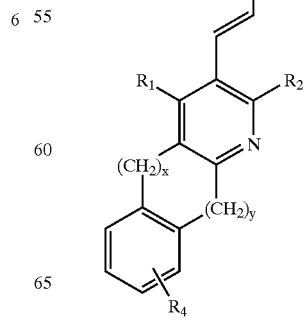
11

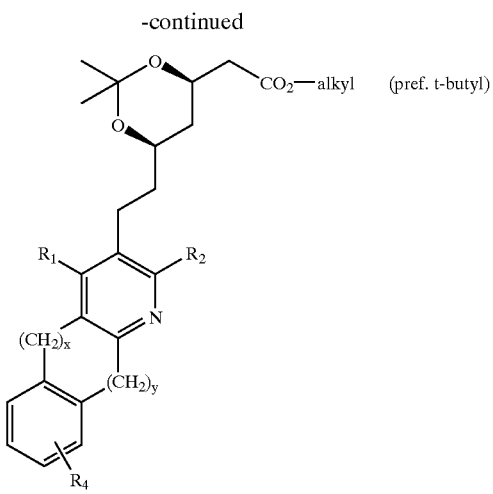

Compounds containing dihydroxy acid HMG-CoA binding domain side chains may be prepared in homochiral form, which is preferred, or may be prepared as racemic mixtures (3S*, 5R*) and may later be resolved to obtain the 3S, 5R isomer.

The compounds of the invention are inhibitors of 3-hydroxy-3-methyl-glutaryl coenzyme A (HMG-CoA) reductase and thus are useful in inhibiting cholesterol biosynthesis and/or in lowering triglycerides, in a manner similar to atorvastatin, pravastatin, simvastatin, lovastatin, cerivastatin, visastatin (or rosuvastatin) (Astra Zeneca ZD4522), fluvastatin, itavastatin (or pitavastatin) and the like.

A further aspect of the present invention is a pharmaceutical composition containing at least one of the compounds of formula I of the present invention in association with a pharmaceutical vehicle or diluent. The pharmaceutical composition can be formulated employing conventional solid or liquid vehicles of diluents and pharmaceutical additives of a type appropriate to the mode of desired administration. The compounds can be administered by an oral route, for example, in the form of tablets, capsules, granules or powders, or they can be administered by a parenteral route in the form of injectable preparations. Such dosage forms contain from 0.1 to 1500 mg of active compound per dosage, for use in the treatment. The dose to be administered depends on the unitary dose, the symptoms, and the age and the body weight of the patient.

The compounds of the present invention can be administered in a similar manner as known compounds suggested for use in inhibiting cholesterol biosynthesis, such as pravastatin, lovastatin, simvastatin, visastatin (or rosuvastatin), atorvastatin, cerivastatin, fluvastatin, itavastatin (or pitavastatin), and the like, in mammalian species such as humans, dogs, cats and the like. Thus, the compounds of the invention may be administered in an amount from about 0.1 to 500 mg in a single dose or in the form of individual doses from 1 to 4 times per day, preferably 0.2 to 100 mg daily or in sustained release form.

The HMG CoA reductase inhibitors of formula I may be employed in combination with all therapeutic agents which are useful in combination with HMG CoA reductase inhibitors.

Thus, where desired, the compounds of structure I may be used in combination with one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-Alzheimer's agents, anti-dementia agents, anti-osteoporosis agents, and/or hormone replacement therapeutic agents, and/or other therapeutic agents, and/or other cardiovascular agents (including anti-anginal agents, anti-arrhythmic agents, anti-atherosclerosis agents, anti-inflammatory agents, anti-platelet agents, anti-heart failure agents), anti-cancer agents, anti-infective agents, hormone replacement agents, growth hormone secretagogues, selective androgen receptor modulators, and/or other therapeutic agents which may be administered orally in the same dosage form or in a separate oral dosage form, or by injection.

The hypolipidemic agent or lipid-lowering agent or other lipid agent or lipid modulating agent which may be optionally employed in combination with the compounds of formula I of the invention may include 1,2,3 or more MTP inhibitors, HMG CoA reductase inhibitors, squalene synthetase inhibitors, PPAR α agonists, PPAR dual α/γ agonists, PPAR δ agonists, fibric acid derivatives, ACAT inhibitors, lipoxygenase inhibitors, cholesterol absorption inhibitors, ileal Na+/bile acid cotransporter inhibitors, upregulators of LDL receptor activity, cholesteryl ester transfer protein inhibitors, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

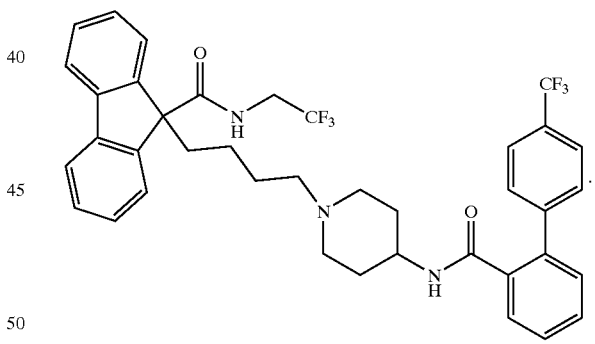

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat.

No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. No. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinylmethyl) phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphoryl-choline (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137 (1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 (ezetimibe) as well as those disclosed in Atherosclerosis 115, 45–63 (1995) and J. Med. Chem. 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795 as well as CETi-1 and JTT-705.

The hypolipidemic agent may be an ileal $Na^+$/bile acid cotransporter inhibitor such as disclosed in Drugs of the Future, 24, 425–430 (1999).

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201;

a beta-lactam cholesterol absorption inhibitor such as disclosed in EP 675714;

an HDL upregulator such as an LXR agonist, a PPAR α-agonist and/or an FXR agonist;

an α-glucosidase inhibitor, an aldose reductase inhibitor and/or an LDL catabolism promoter such as disclosed in EP 1022272;

a sodium-proton exchange inhibitor such as disclosed in DE 19622222;

an LDL-receptor inducer or a steroidal glycoside such as disclosed in U.S. Pat. No. 5,698,527 and GB 2304106;

an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E;

isoniazid as disclosed in WO 97/35576;

a cholesterol absorption inhibitor, an HMG-CoA synthase inhibitor, or a lanosterol demethylase inhibitor as disclosed in WO 97/48701;

a PPAR δ agonist for treating dyslipidemia;

or a sterol regulating element binding protein-I (SREBP-1) as disclosed in WO 2000/050574, for example, a sphingolipid, such as ceramide, or neutral sphingomyelenase (N-SMase) or fragment thereof.

Preferred hypolipidemic agents are pravastatin, lovastatin, simvastatin, atorvastatin, fluvastatin, cerivastatin, pitavastatin and rosuvastatin, as well as niacin and/or cholestagel.

The above-mentioned U.S. patents are incorporated herein by reference. The amounts and dosages employed will be as indicated in the Physician's Desk Reference and/or in the patents set out above or as otherwise known in the art.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent or other lipid agent or lipid modulating agent will be as disclosed in the various patents and applications discussed above.

The dosages and formulations for the other hypolipidemic agent or other lipid agent or lipid modulating agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The anti-atherosclerotic agent includes a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties," Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The antidiabetic agent which may be optionally employed in combination with the HMG-CoA reductase inhibitor of formula I may be 1,2,3 or more antidiabetic agents or antihyperglycemic agents including insulin secretagogues or insulin sensitizers, which may include biguanides, sulfonyl ureas, glucosidase inhibitors, aldose reductase inhibitors, PPAR γ agonists such as thiazolidinediones, PPAR δ agonists (such as fibric acid derivatives), PPAR δ antagonists or agonists, aP2 inhibitors, PPAR α/γ dual agonists, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05:1 to about 10:1.

The sulfonyl urea and PPAR γ agonists in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) or mimetic such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the PPAR anti-diabetic agent may be employed in amounts within the range from about 0.01 to about 2000 mg/day which may be administered in single or divided doses one to four times per day.

Where present insulin and other anti-diabetic agents as set out above may be employed in formulations, amounts and dosing as indicated by the Physician's Desk Reference.

Where present GLP-1 peptides or mimetics may be administered in oral buccal formulations, by nasal administration or parenterally as described in U.S. Pat. Nos. 5,346,701 (TheraTech), 5,614,492 and 5,631,224 which are incorporated herein by reference.

The antidiabetic agent or other lipid agent may also be a PPAR modulator such as a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. application Ser. No. 09/664,598, filed Sep. 18, 2000, (attorney file LA29) the disclosure of which is incorporated herein by reference, employing dosages as set out therein, which compounds designated as preferred are preferred for use herein.

The antidiabetic agent may be an SGLT2 inhibitor such as disclosed in U.S. application Ser. No. 09/679,027, filed Oct. 4, 2000 (attorney file LA49), employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000 (attorney file LA27), employing dosages as set out herein. Preferred are the compounds designated as preferred in the above application.

The antidiabetic agent may be a DP4 inhibitor such as disclosed in application Ser. No. 09/788,173, filed Feb. 16, 2001 (attorney file LA50), WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide or Starlix® (Novartis) nateglinide (Novartis) or KAD1229 (PF/Kissei), with repaglinide being preferred.

The antidiabetic compound may be a melanocortin receptor agonist such as a spiropiperidine as disclosed in WO 99/64002.

The HMG CoA reductase inhibitor of formula I will be employed in a weight ratio to the meglitinide, PPAR modulator such as a PPAR γ agonist, PPAR α agonist, PPAR δ agonits or antagonist, PPAR α/γ dual agonist, aP2 inhibitor, DP4 inhibitor or SGLT2 inhibitor or other antidiabetic agent within the range from about 0.01:1 to about 100:1, preferably from about 0.05:1 to about 10:1.

The other type of therapeutic agent which may be optionally employed with the HMG CoA reductase inhibitor of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor beta drug, a PTP-1B inhibitor, an anorectic agent, a PPAR modulator including PPAR γ antagonists, PPAR α agonists, PPAR δ antagonists, a CCKA agonist, a leptin inhibitor such as a leptin receptor activator, a neuropeptide Y antagonist, a melanocortin-4-receptor (MC4R) agonist, a fatty acid oxidation upregulator or inducer (such as Famoxin® Genset).

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The neuropeptide Y antagonists which may be optionally employed in combination with a compound of formula I include those described in WO 0113917 (BMS) or in U.S. Pat. No. 6,218,408 (Synaptic) and in WO 0114376 (Banyu).

The lipase inhibitor which may optionally be employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO99/00353 (KaroBio), GB98/284425 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The CCKA agonists which may be employed herein include Glaxo-SmithKline's GI-181,771 and Sanofi's SR146,131.

The PTP-1B inhibitor which may be an anti-oesity and/or an antidiabetic agent include those disclosed in WO 99/585, 521, WO 99/58518, WO 99/58522 and WO 99/61435.

The anti-obesity agent employed may also be Pfizer's P57 or CP-644,673 (licensed from Phytopharm).

The various anti-obesity agents described above may be employed in the same dosage form with the compound of formula I or in different dosage forms, in dosages and regimens as generally known in the art or in the PDR.

The antihypertensive agents which may be employed in combination with the HMG CoA reductase inhibitors of the invention include ACE inhibitors, angiotensin II receptor antagonists, NEP inhibitors such as candoxatril, NEP/ACE inhibitors, as well as calcium channel blockers (such as verapamil and amlodipine besylate), T-channel calcium antagonists (such as mibefradil), β-adrenergic blockers, diuretics, α-adrenergic blockers (such as doxazosin mesylate and terazosin HCl), dual action receptor antagonists (DARA), heart failure drugs such as digoxin, and other types of antihypertensive agents.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(l-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432, 971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and Curr. Ther. Res. 40:74 (1986); Ru 44570 (Hoechst) disclosed in Arzneimittelforschung 34:1254 (1985), cilazapril (Hoffman-LaRoche) disclosed in J. Cardiovasc. Pharmacol. 9:39 (1987); R 31–2201 (Hoffman-LaRoche) disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. clin. Pharmacol. 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxycarbonyl)-3-phenylpropyl]amino]-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, U.S. Pat. No. 5,552,397, U.S. Pat. No. 5,504,080, U.S. Pat. No. 5,612,359,U.S. Pat. No. 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, gemopatrilat ([S[(R*,R*)]-hexahydro-6-[(2-mercapto-1-oxo-3-phenylpropyl)amino]-2,2-dimethyl-7-oxo-1H-azepine-1-acetic acid) and CGS 30440.

The angiotensin II receptor antagonist (also referred to herein as angiotensin II antagonist or AII antagonist) suitable for use herein includes, but is not limited to, irbesartan, losartan, valsartan, candesartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist will be as set out in the latest edition of the Physician's Desk Reference (PDR).

Dual action receptor antagonists (DARA) suitable for use herein include those disclosed in U.S. application Ser. No. 09/513,779, filed Feb. 25, 2000, and Ser. No. 09/604,322, filed Jun. 26, 2000.

Other examples of preferred antihypertensive agents suitable for use herein include omapatrilat (Vanlev®), gemopatrilat, amlodipine besylate (Norvasc®), prazosin HCl (Minipress®), verapamil, nifedipine, diltiazem, felodipine, nisoldipine, isradipine, nicardipine, beta blockers such as nadolol, atenolol (Tenormin®), sotalol, terazosin, doxazosin, carvedilol, and propranolol, and clonidine HCl (Catapres®).

Diuretics which may be employed in combination with compounds of formula I include hydrochlorothiazide, torasemide, furosemide, spironolactone, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antihypertensive agents, diuretics and antiplatelet drugs may be employed in amounts as indicated in the PDR. Ifetroban may be employed in amounts as set out in U.S. Pat. No. 5,100,889.

Anti-Alzheimer's agents or anti-dementia agents suitable for use herein with the HMG CoA reductase inhibitors of the invention include tacrine HCl (Cognex®) and donepezil (Aricept®), as well as γ-secretase inhibitors, β-secretase inhibitors and/or antihypertensive agents. Dosages employed will be as set out in the PDR.

Antiosteoporosis agents suitable for use herein in combination with the HMG CoA reductase inhibitors of the invention include parathyroid hormone or bisphosphonates, such as MK-217 (alendronate) (Fosamax®) as well as Ca receptor agonists and progestin receptor agonists. Dosages employed will be as set out in the PDR.

The hormone replacement therapeutic agents, where present, will be employed in dosages as set out in the latest edition of the PDR. Examples of such agents include selective estrogen receptor modulators (SERMs) such as raloxifen, tamoxifen or lasoxifen.

The HMG CoA reductase compound of the invention may also be employed in combination with a tyrosine kinase inhibitor such as disclosed in WO 2000/053605;

the selective androgen receptor modulator suitable for use herein may be LGD-2226 (Ligand);

the antiarrhythmic agents suitable for use herein include β-blockers as set out herein including sotalol and amioderome, calcium channel blockers as set out herein including verapamil, nifedipine, amlodipine-besylate, and diltiazem, which may also be used in combination with a debrillator device such as a pace maker;

coenzyme Q sub. 10 such as disclosed in U.S. Pat. No. 5,316,765, 4,933,165, 4,929,437;

an agent that upregulates type III endothelial cell nitric acid syntase such as disclosed in WO 2000/003746;

a chondroprotective compound such as a polysulfated glycosaminoglycan (PSGAG), glucosamine, chondroitin sulfate (CS), hyaluronic acid (HA), pentosan polysulfate (PPS), doxycycline or minocycline, such as disclosed in EP 970694;

a cyclooxygenase (COX)-2 inhibitor, such as celecoxib (Celebrex® (Searle)) or rofecoxib (Vioxx® (Merck)) or a glycoprotein IIa/IIIb receptor antagonist such as disclosed in WO 99/45913 and tirofiban or abciximab;

a 5-HT reuptake inhibitor such as disclosed in WO 99/44609;

anti-anginal agents such as vasodilators, for example, isosorbide dinitrate, or nitroglycerin;

a growth hormone secretagogue such as disclosed in U.S. application Ser. No. 09/662,448, filed Sep. 14, 2000, and U.S. Provisional application 60/203,335, filed May 11, 2000, and MK-677 (Merck), Pfizer's CP-424391 and Lilly's LY 444,711;

anti-atherosclerosis agents such as ACAT inhibitors and lipoxygenase inhibitors as described herein and phospholipase A-2 inhibitors such as S-3013 and SB-435,495 (which are also anti-inflammatory agents);

anti-infective agents such as quinolones, for example, ciprofloxacin, ofloxacin, and Tequin® (Bristol-Myers Squibb), macrolides such as erythromycin and clarithromycin (Biaxin® (Abbott)), and azithromycin (Zithromax (Pfizer)); or an immunosuppressant (for use in transplantations) such as cyclosporine, mycophenolate mofetil, azathioprine and the like.

As used herein, the phrase "antineoplastic agent" refers to compounds which prevent cancer cells from multiplying. In general, the antineoplastic agents used herein prevent cancer cells from multiplying by: (1) interfering with the cell's ability to replicate DNA, or (2) inducing apoptosis in the cancerous cells.

Examples of antineoplastic agents which are suitable for use in combinations of this invention include, but are not limited to, microtuble-stabilizing agents such as the taxanes, for example, paclitaxel (also known as Taxol®), docetaxel (also known as Taxotere®), 7-O-methylthiomethylpaclitaxel (disclosed in U.S. Pat. No. 5,646,176), 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 60/179,965 filed on Feb. 3, 2000, and example 17 herein), C-4 methyl carbonate paclitaxel (disclosed in WO 94/14787), the epothilone, such as epothilone A, epothilone B, epothilone C, epothilone D, desoxyepothilone A, desoxyepothilone B, [1S-[1R*,3R*(E), 7R*, 10S*, 11R*, 12R*, 16S*]]-7,11-dihydroxy-8,8,10,12, 16-pentamethyl-3-[1-methyl-2-(2-methyl-4-thiazolyl) ethenyl]-4-aza-17-oxabicyclo[14.1.0]heptadecane-5,9-dione (disclosed in WO 99/02514), [1S-[1R*,3R*(E),7R*, 10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]-heptadecane-5,9-dione (disclosed in U.S. Ser. No. 09/506,481 filed on Feb. 17, 2000, and examples 7 and 8 herein), and derivatives thereof; microtuble-disruptor agents; alkylating agents; antimetabolites; epidophyllotoxin; an antineoplastic enzyme; a topoisomerase inhibitor; procarbazine; mitoxantrone; platinum coordination complexes; biological response modifiers; growth inhibitors; hormonal/antihormonal therapeutic agents; and haematopoietic growth factors.

Other classes of antineoplastic agents suitable for use in the method of the present invention include, but are not limited to, the anthracycline family of drugs, the vinca drugs, the mitomycins, the bleomycins, the cytotoxic nucleosides, discodermolide, the pteridine family of drugs, diynenes, aromatase inhibitors, and the podophyllotoxins. Particularly useful members of those classes not previously mentioned include, for example, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, and the like. Other useful antineoplastic agents include estramustine, cisplatin, carboplatin, cyclophosphamide, bleomycin, tamoxifen, ifosfamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, and interleukins.

It will be appreciated that unless otherwise specified the dosage regiment for therapeutic agents used in combination with the compounds of the invention will be as specified in the PDR.

In carrying out the method of the invention for treating hypercholesterolemia, hyperlipidemia, hyperlipoproteinemia, hypertriglyceridemia, or atherosclerosis, and related diseases, or Alzheimer's disease or osteoporosis, or other disclosures as set out hereinbefore, a pharmaceutical composition will be employed containing the compounds of structure I, with or without other cholesterol lowering agents, osteoporosis agents, Alzheimer's agents, antidiabetic agent(s) and/or antihyperlipidemic agent (s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 0.1 to about 500 mg of a compound of formula I. The dose for adults is preferably between 0.5 and 1,000 mg per day, which can be administered in a single dose or in the form of individual doses from 1–4 times per day and also single dose once weekly (5 to 1000 mg).

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following abbreviations are employed in the Examples and elsewhere herein:

Ph=phenyl
Bn=benzyl
i-Bu=iso-butyl
Me=methyl
Et ethyl
TMS=trimethylsilyl
FMOC=fluorenylmethoxycarbonyl
Boc=tert-butoxycarbonyl
Cbz=carbobenzyloxy or carbobenzoxy or benzyloxycarbonyl
DIPEA=diisopropyl ethylamine
PTSH=N-phenylthiotetrazole
$PPh_3$=triphenylphosphine
NMO=methylmorpholine N-oxide
TPAP=tetrapropylammonium perruthenate
DEAD=diethyl azodicarboxylate
HOAc or AcOH=acetic acid
TFA=trifluoroacetic acid
$Et_2NH$=diethylamine
NMM=N-methyl morpholine
n-BuLi=n-butyllithium
Pd/C=palladium on carbon
$PtO_2$=platinum oxide
MTBE=methyl t-butyl ether
DI water=dionized water
TEA=triethylamine
EDAC=3-ethyl-3'-(dimethylamino)propyl-carbodiimide hydrochloride (or 1-[(3-(dimethyl)amino)propyl])-3-ethylcarbodiimide hydrochloride)
HOBT or $HOBT.H_2$=1-hydroxybenzotriazole hydrate
HOAT=1-hydroxy-7-azabenzotriazole
PyBOP reagent=benzotriazol-1-yloxy-tripyrrolidino phosphonium hexafluorophosphate
$LiN(TMS)_2$=Libis(trimethylsilyl)amide
DIBAL=diisobutylaluminum hydride
LDA=lithium diisopropylamide
DMPU=1,3-dimethyl-3,4,5,6-tetrahydro-2(1H)-pyrimidinone
AcCN=acetonitrile
LiHMDS=lithium bis(trimethylsilyl)amide
NaHMDS=sodium bis(trimethylsilyl)amide
Red-AL=sodium bis(2-methoxyethoxy)aluminum hydride
mCPBA=m-chloro-p-benzoic acid
alloc=allyloxycarbonyl
FMOC=fluorenylmethyloxycarbonyl
min=minute(s)
h or hr=hour(s)
L=liter
mL=milliliter
μL=microliter
g=gram(s)
mg=milligram(s)
mol=moles
mmol=millimole(s)
meq=milliequivalent
RT, rt=room temperature sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point
Bp=boiling point The following Examples represent preferred embodiments of the invention. Unless otherwise indicated, all temperatures are in degrees Centigrade.

EXAMPLE 1

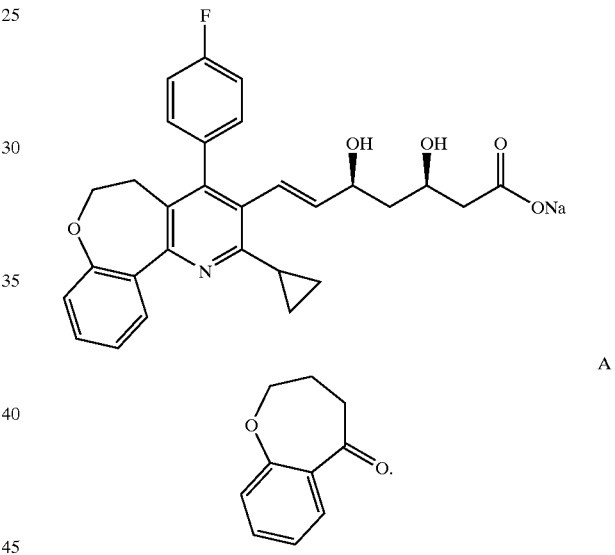

A

A mixture of polyphosphoric acid (82.9 g) and dry o-xylene (30 ml) was heated to 105–110° C. in an oil bath, treated with a solution of 4-phenoxybutyric acid (25 g, 0.137 mole) in dry o-xylene (110 ml) and stirred at 105–110° C. for 2 hours. The reaction mixture was cooled to room temperature over a 2-hour period, poured into ice-water (180 ml), then extracted with ether (3×150 ml). The combined organic extracts (rust-colored) were washed with water (2×80 ml) and brine (80 ml), dried (anhydrous $Na_2SO_4$), filtered, evaporated to dryness and evaporated once from hexanes (500 ml). The residue was dried in vacuo for 48 hours to give a reddish-brown syrup (27.19 g) which was divided into two portions, chromatographing each portion on a silica gel column, (EM, 2¼"×10") to give a light amber syrup (10.792 g). Trituration of an impure fraction with ether (3×25 mL) gave an additional 1.98 g of product. Yield: 12.77 g, amber syrup; 58%. Rf 0.38 (Silica gel; EtOAc:Hexane-1:4; UV).

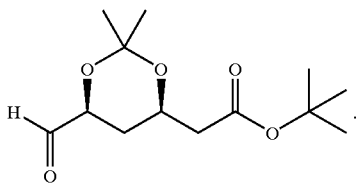
A(1)

An oven-dried 3-neck 1-L flask equipped with temperature sensor probe, 125-mL constant pressure addition funnel and septum was charged with dry $CH_2Cl_2$ (300 mL) and dry DMSO (20.9 mL, 0.2944 mol, 2.5 equiv) under argon atmosphere; cooled to −75° C. Oxalyl chloride (13.6 mL, 0.156 mol, 1.32 equiv) was added neat via syringe dropwise over 15 min (temperature rose to −66° C.), and then let stir additional 15 min. A solution of the alcohol 2-[(4R,6S)-6-(hydroxymethyl)-2,2-dimethyl-1,3-dioxan-4-yl]acetic acid t-butyl ester (30.66 g, 0.1178 mol, 1 equiv) in dry $CH_2Cl_2$ (80 mL) was added dropwise from the addition funnel over 30 min (temperature rose to −68° C.). The resulting white mixture was stirred for 70 min at −76° C, then triethylamine (82 mL, 0.5889 mol, 5 equiv) was added dropwise from addition funnel over 35 min (temperature rose to −65° C.), then the light yellow mixture was stirred vigorously at −76° C. TLC ($SiO_2$, 20% $EtOAc/CH_2Cl_2$, Rf=0.52). After 30 min, the cooling bath was removed and the reaction was quenched by slowly adding cold 20% aq $KH_2PO_4$ (35 mL), followed by cold $H_2O$ (300 mL); and then let stir 15 min (temperature rose to −7° C.). The reaction was poured into a 2-L separatory funnel and extracted with hexanes (500 mL). The organic extract was washed with cold 10% aq $KH_2PO_4$ (3×300 mL) and saturated aqueous NaCl (300 mL). The organic was dried over anhydrous $Na_2SO_4$, filtered and concentrated in vacuo to give yellow oil. Purification by $SiO_2$ flash chromatography (10 cm×20 cm column) with 35:65 EtOAc/Hexanes afforded the title compound as a white solid (22.2 g, 0.0859 mol, 73%):

$^1$H NMR ($CDCl_3$) δ 1.267–1.465 (m, 16H), 1.802 (dd, J=12.7 Hz, 2.2 Hz, 1H), 2.290–2.464 (m, 2H), 4.314 (d, J=18.4 Hz, 2H), 9.555 (d, J=1.3 Hz, 1H).

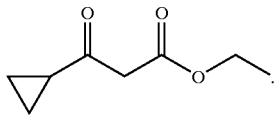
A(2)

To a slurry of NaH (19.20 g, 480 mmol) and diethyl carbonate (80 mL) in a 3-neck 1L round bottom flask at room temperature was added a solution of cyclopropyl methylketone (23.5 mL, 238 mmol) in $Et_2O$ (30 mL). Approximately 10% of the solution was added, and then 0.25 mL of EtOH was added to the reaction slurry. Addition of the remaining ketone solution continued with light gas evolution. After addition of all of the ketone solution, the reaction became quite exothermic with vigorous $H_2$ evolution. The reaction mixture was cooled periodically with an ice-bath to keep the temperature around 35° C. to 50° C. After one hour, gas evolution had ceased and the reaction mixture was stirred at room temperature for 2 h. The reaction mixture was cooled in an ice-bath, diluted with $Et_2O$ (200 mL), and treated with 1 N HCl with some ice to adjust to around pH 3. The reaction mixture was extracted with $Et_2O$ (3×150 mL). The $Et_2O$ extracts were combined, washed with saturated aqueous $NaHCO_3$ (200 mL), $H_2O$ (200 mL) and brine (200 mL), and dried ($Na_2SO_4$), filtered and concentrated under reduced pressure to give a yellow oil. The oil was distilled under vacuum to give the title compound as a colorless oil, 28.5 g, 77%. B.p. 94–96° C./8 mmHg.

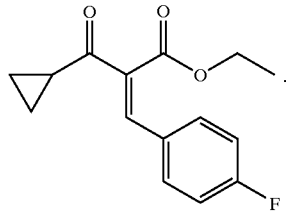
A(3)

To a stirred solution of part A(2) compound (28.24 g, 181 mmol) in benzene (128 mL) was added 4-fluorobenzaldehyde (19.4 mL, 181 mmol), HOAc (0.31 mL, 5.4 mmol) and piperidine (1.8 mL, 18.2 mL). The reaction mixture was heated at reflux and azeotrope was collected with a Dean-Stark trap. After 16 h, the reaction was cooled to room temperature, diluted with $Et_2O$ (250 mL), washed with aqueous 0.5 N HCl, saturated aqueous $NaHCO_3$, $H_2O$ and brine, and then dried ($Na_2SO_4$), filtered and concentrated under reduced pressure. Purification by flash chromatography (1:10 EtOAc/hexane) gave the title compound as a light yellow oil, 29 g, 61% yield.

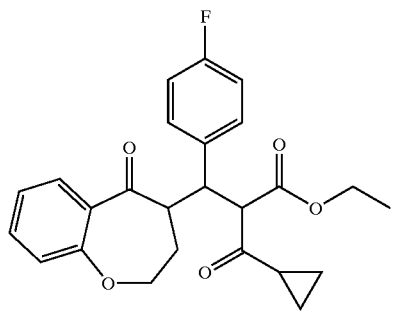
B

A solution of compound of Part A (7.21 g, 40.9 mmol) in dry THF (5.0 ml) was added to a −78° C. solution of lithium bis(trimethylsilyl)amide (1.0 M in THF; 49 ml, 49 mmol) in dry THF (25 ml) and stirred at −78° C. under argon for 1 hour. The reaction mixture was treated with a solution of Example 1 Part A(3) compound (7.15 g, 27.3 mmoles), in dry THF, stirred at −78° C. for 30 minutes then at 0° C. for 30 minutes. The reaction mixture was quenched at 0° C. by the dropwise addition of glacial acetic acid (5 ml) and the resulting slurry was stirred at room temperature for another 5 minutes then poured slowly into an ammonium chloride solution (25%, 140 ml). The bright yellow solution was extracted with ether (2×100 ml) and the combined organic extracts were washed with water (2×25 ml) and brine (25 ml), dried (anhydrous $Na_2SO_4$), filtered, evaporated to dryness and dried in vacuo to give the crude product mixture as a yellow oil (17.16 g).

C

A mixture of crude Part B compound (17.0 g, 27.3 mmol), ammonium acetate (9.34 g, 120 mmol) and copper acetate monohydrate (20.54 g, 101 mmol) in glacial acetic acid (100 ml) was refluxed under argon for 19 hours. The mixture was poured into an ice-cold solution of concentrated ammonium hydroxide (85 ml) in water (170 ml) and the bright blue solution was extracted with ether (3×200 ml). The combined organic extracts were washed with water (2×80 ml) and brine (80 ml), dried (anhydrous $Na_2SO_4$), filtered, evaporated to dryness, and dried in vacuo. The crude product (14 g, brown syrup) was chromatographed in two batches, each on a silica gel column (EM, 2¼"×10") to give the desired product as an off-white solid (4.161 g). An additional 931 mg of product was obtained from chromatography of mixed fractions. Yield: 5.092 g, 46% from compound A). Rf 0.53 (Silica gel; EtOAc:Hexane-1:4; UV)

D

A solution of Part C compound (2.515 g, 6.23 mmol) in dry THF (30 ml) was cooled to 0° C. (ice-water bath), treated dropwise with lithium aluminum hydride (1.0 M in THF; 12.5 ml, 12.5 mmol), stirred at 0° C. for 30 minutes then at room temperature for 3 hours. The reaction mixture was cooled to 0° C., treated successively with water (0.5 ml), 15% NaOH (0.5 ml) and water (1.5 ml), stirred at room temperature for 5 minutes then diluted with ethyl acetate (50 ml). The slurry was filtered through a Celite® pad, washing the pad well with ethyl acetate (3×25 ml). The clear filtrate was evaporated to dryness and dried in vacuo to give the title product. Yield: 2.386 g, white foam (100%). Rf 0.15 (Silica gel; EtOAc:Hexane-1:4; UV)

E

A solution of Part D compound (2.27 g, 6.23 mmol) in dry dichloromethane (45 ml) was cooled to 0° C. (ice-water bath) and treated dropwise with phosphorus tribromide (1.0 M in dichloromethane; 12.5 ml, 12.5 mmol). The ice bath was removed and the reaction mixture was stirred at room temperature for 30 minutes after which it was re-cooled to 0° C. and treated dropwise with saturated sodium bicarbonate (70 ml). The mixture was then warmed to room temperature and extracted with ethyl acetate (2×100 ml). The combined organic extracts were washed with water (2×50 ml) and brine (50 ml), re-extracting each aqueous wash with dichloromethane (100 ml). The organic extracts were dried (anhydrous sodium sulfate), filtered, evaporated to dryness and dried in vacuo to give the title product as a white solid. Yield: 2.503 g, (94%). m.p.=169–171° C. Rf 0.58 (Silica gel; EtOAc:Hexane-1:4; UV).

F

A solution of diethyl phosphite (0.88 ml, 6.83 mmoles) in dry THF (10 ml) was cooled to -10° C. (acetonitrile-dry ice bath), treated with sodium (bistrimethylsilyl)amide (1.0 M in THF; 6.7 ml, 6.7 mmol) and stirred at -10° C. for 30 minutes. The cooled solution was treated with a solution of Part E compound (2.41 g, 5.68 mmol) in dry THF (20 ml), stirred at -10° C. for 1.0 hour then quenched at -10° C. with water (14 ml). The solution was extracted with ethyl acetate (2×75 ml) and the combined organic extracts washed with 1.0 M hydrochloric acid (8.0 ml) and brine (10 ml), dried (anhydrous sodium sulfate), filtered, evaporated to dryness and dried in vacuo. The crude product (3.12 g, syrup) was chromatographed on a silica gel column (EM, 5.5 cm×12.5 cm) to give the title compound as a syrup. Yield: 2.34 g (85.5%). Rf 0.33 (Silica gel; EtOAc-Hexane-1:1; UV).

G

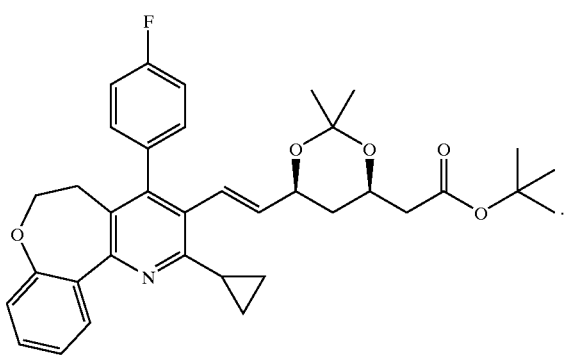

I

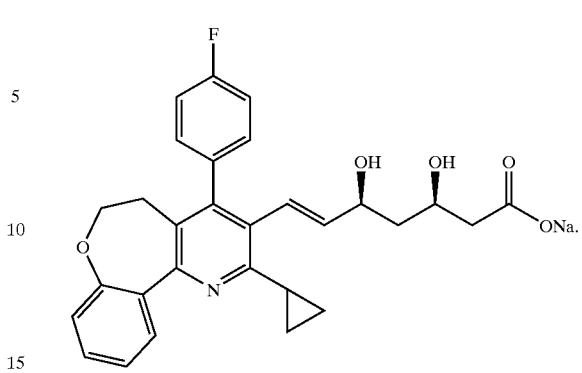

A solution of Part F compound (2.29 g, 4.756 mmol) in dry THF (20 ml) was cooled to −78° C., treated with 2.37 M n-butyllitium (2.41 ml, 5.71 mmol) and stirred at −78° C. for 40 minutes. The solution was treated dropwise via cannula with a −78° C. solution of Part A(l) compound (2.36 g, 9.15 mmol) in dry THF (10 ml), keeping both solutions at −78° C. at all times. The reaction mixture was stirred at −78° C. for 1.0 hr, −10° C. for 1.0 hr and at room temperature for 5 hr, quenched with 25% ammonium chloride solution (12 ml) then extracted with ethyl acetate (2×100 ml). The combined organic extracts were washed with 25% ammonium chloride solution (12 ml) and brine (12 ml), dried (anhydrous sodium sulfate), filtered, evaporated to dryness and dried in vacuo. The crude product yellow syrup was chromatographed on a silica gel column (EM, 2¼"×10") to afford the title compound as a syrup. Yield: 878 mg (32%). Rf 0.37 (Silica gel; EtOAc:Hexane-1:4; UV).

A solution of Part H compound (550 mg, 1.17 mmol) in dry THF (10 ml) was treated with 1.0 N NaOH (1.46 ml; 1.46 mmol) and stirred at room temperature for 10 minutes. The reaction mixture was evaporated to dryness and the residual solid was dissolved in a mixture of water (8.7 ml) and 1.0 N sodium hydroxide (70 ul). The solution was eluted on an SP207 column (Na+ form; 1.5"×4"), eluting the column with water (200 ml), 10% $CH_3CN/H_2O$ (200 ml), 20% $CH_3CN/H_2O$ (100 ml) and 50% $CH_3CN/H_2O$ (200 ml). The desired fractions were combined and evaporated to dryness. The semi-solid obtained was dissolved in water (300 ml) and lyophilized to give the title compounds as a white solid. Yield: 583 mg (95%) Rf 0.48 (Silica gel; $CH_2Cl_2$:MeOH:HOAc-18:1:1; UV).

Analysis for $C_{29}H_{26}FNO_4Na.0.8\ H_2O$ (MW 525.94):
Calc'd: C, 66.23; H, 5.29; N, 2.66; F, 3.61
Found: C, 66.37; H, 5.30; N, 2.62; F, 3.91

Alternate Procedure for Example 1 Part G Compound

H

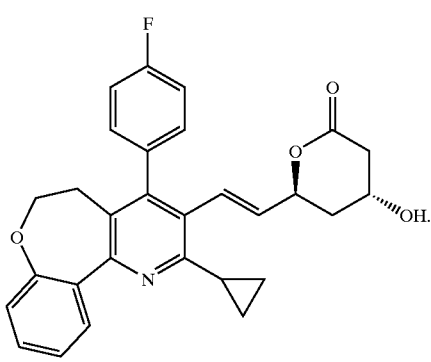

G(1)

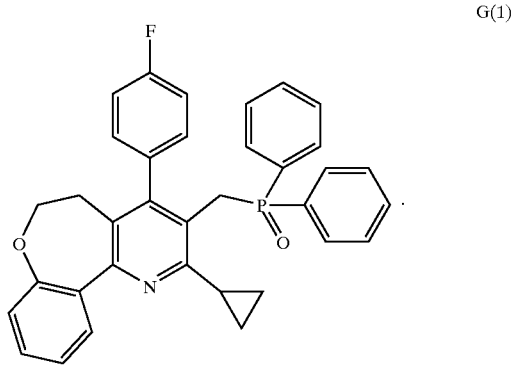

A solution of Part G compound (850 mg, 1.45 mmol) in dry dichloromethane (20 ml) was cooled to 0° C., treated with trifluoroacetic acid (1.85 ml, 24 mmol), stirred at 0° C. for 5 minutes, then at room temperature for 4.5 hours. The reaction mixture was poured slowly into a 1 L flask containing ethyl acetate (300 ml) and saturated sodium bicarbonate (40 ml), rinsing the flask with ethyl acetate (50 ml). The mixture was stirred well and the phases separated, washing the organic phase with saturated sodium bicarbonate (25 ml) and brine (25 ml). The organic phase was dried over anhydrous sodium sulfate, filtered, evaporated to dryness and dried in vacuo. The crude product mixture was chromatographed on a silica gel column (EM, 1.5"×12") to give the desired compound as a syrup. Yield: 570 mg (83%). Rf 0.23 (Silica gel; EtOAc:Hexane-1:1; UV)

The Example 1 Part E bromide (13.03 g, 0.027 mol, 1 equiv) and $Ph_2POEt$ (6.5 mL, 0.0297 mol, 1.1 equiv) were heated at reflux in anhydrous toluene (200 mL) under an argon atmosphere. The reaction became a thick yet stirrable white mixture after about 10 min. The reaction was complete after 1 hr by tlc ($SiO_2$, 30% $EtOAc/CH_2Cl_2$, product Rf=0.34). The mixture was cooled to 0°, and the white precipitate was collected by vacuum filtration, washed with hexanes (2×50 mL), and dried in vacuo (14.8 g, 0.027 mol, 100%): HPLC (Shimadzu, YMC S-5 C18 4.6×50 mm column, 4 min gradient @ 4 mL/min, UV detection 220 nM; start % B=50, final % B=100; A=10:90 MeOH/$H_2O$+0.2% $H_3PO_4$, B=90:10 MeOH/$H_2O$+0.2% $H_3PO_4$) R.T.=3.70 min (100%);

$^1$H NMR (CDCl$_3$) δ 0.712–0.760 (m, 2 H), 1.10–1.14 (m, 2 H), 2.163–2.228 (m, 1 H), 2.3211 (t, J=6.2 Hz, 2 H), 3.850

(d, J=14 Hz, 2 H), 4.2568 (t, J=6.2 Hz, 2 H), 6.779 (dd, J=8.3 Hz, 5.3 Hz, 2 H), 6.9542 (t, J=8.3 Hz, 2 H), 7.070 (d, J=7.9 Hz, 1 H), 7.257 (t, J=7.5 Hz, 1 H), 7.334–7.421 (m, 9 H), 7.469–7.521 (m, 2 H), 7.822 (d, J=7.5 Hz, 1 H); MS m/z 546 (M+H)$^+$.

G(2)

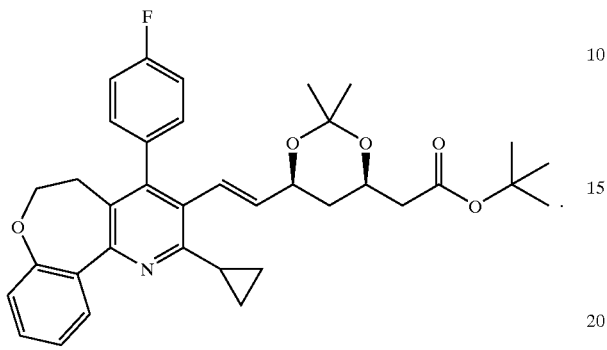

A flame-dried 250-mL flask was charged with Part G(1) compound (14.82 g, 27.2 mmol, 1 equiv), chased with anhydrous toluene (2×50 mL), dried over high-vacuum and filled with argon. THF (150 mL) was added and the partial slurry was cooled to 0° C. A 2.5 M solution of n-BuLi in hexanes (11.4 mL, 0.0285 mol, 1.05 equiv) was added dropwise to the vigorously stirred mixture over a period of 40 min. The resulting green colored solution was then stirred for 1 hr at 0° C. The aldehyde Example A(l) compound (8.42 g, 0.0326 mol, 1.2 equiv) in a flame-dried 500-mL flask (material previously chased with anhydrous toluene, 3×20 mL) under an argon atmosphere was dissolved in dry THF (75 mL) and cooled to –78° C. The phoshine anion solution was added dropwise to the aldehyde via cannula over a period of 45 min, then the dark blue colored solution was stirred at –78° C. for 1.5 hr. The mixture was let warm to room temperature over a 2 hr period; the initially blue solution became a dark brick-red color and finally a light orange color. TLC (SiO$_2$, 5% EtOAc/CH$_2$Cl$_2$, product Rf=0.37). The reaction was quenched with half-saturated aqueous NaCl (200 mL) and extracted with Et$_2$O (300 mL); the organic was washed with H$_2$O (2×100 mL) and saturated aqueous NaCl (100 mL). The organic layer was dried over anhydrous Na$_2$SO$_4$, filtered and concentrated in vacuo. Purification by SiO$_2$ flash chromatography (10 cm×25 cm) with 2% EtOAc/CH$_2$Cl$_2$ (2 L), 3% EtOAc/CH$_2$Cl$_2$ (2 L), 5% EtOAc/CH$_2$Cl$_2$ (1 L), 7% EtOAc/CH$_2$Cl$_2$ (1 L), and 10% EtOAc/CH$_2$Cl$_2$ (1 L) afforded Part G(2) compound (the same as Example 1 Part G compound) as a white solid (11.13 g, 0.019 mol, 70%): HPLC (Shimadzu, YMC S-5 C18 4.6×50 mm column, 4 min gradient @ 4 mL/min, UV detection 220 nM; start %B=70, final % B=100; A=10:90 MeOH/H$_2$O+0.2% H$_3$PO$_4$, B=90:10 MeOH/H$_2$O+0.2% H$_3$PO$_4$) R.T.=4.36 min (100%);

$^1$H NMR (CDCl$_3$) δ 0.928–1.039 (m, 3 H), 1.191–1.368 (m, 6 H), 1.4384 (s, 3 H), 1.4483 (s, 9 H), 2.225–2.431 (m, 3 H), 2.4782 (t, J=6.2 Hz, 2 H), 4.188–4.334 (m, 2 H), 4.3667 (t, 2 H), 5.5846 (dd, J=16.2 Hz, 5.7 Hz, 1 H), 6.342 (d, J=16.2 Hz, 1 H), 7.0663–7.1356 (m, 5 H), 7.257 (t, J=7.5 Hz, 1 H), 7.3538 (t, J=7.5 Hz, 1 H), 7.828 (d, J=7.5 Hz, 1 H); MS (FAB) m/z 586 (M+H)$^+$.

EXAMPLE 2

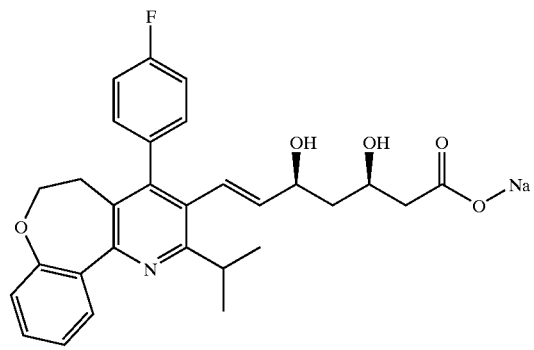

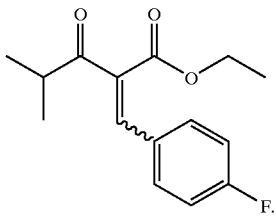

A

A mixture of p-fluorobenzaldehyde (4.939 g, 0.039 mol, 1 equiv), ethyl isobutyrylacetate (6.495 g, 0.039 mol, 1 equiv), piperidine (0.395 mL, 3.91 mmol, 0.1 equiv), and glacial acetic acid (0.070 mL, 1.22 mmol, 0.03 equiv) in anhydrous benzene (30 mL) was heated at reflux with a Dean-Stark trap to collect H$_2$O. After 20 hrs, the reaction was cooled to rt. The yellow reaction mixture was diluted with Et$_2$O (50 mL) and washed with 0.5N aq HCl, satd. aq NaHCO$_3$, H$_2$O, and satd. aq NaCl. The organic extract was dried over anhydrous Na$_2$SO$_4$, vacuum filtered and the filtrate concentrated by rotary evaporation in vacuo to yellow oil. Vacuum distillation afforded the desired product as a light yellow oil (8.575 g, 0.0324 mol, 83%): bp 107–115° C. (0.225 mm Hg);

$^1$H NMR (CDCl$_3$) δ 1.047 and 1.160 (d's, J=6.6 Hz, 6H, 1.4:1 ratio), 1.260 and 1.296 (t's, J=7.1 Hz, 3H, 1:1.4 ratio), 2.674 and 3.140 (m's, J=7 Hz, 1H, 1.4:1 ratio), 4.245–4.324 (m, 2H), 7.010–7.074 (m, 2H), 7.346–7.448 (m, 2H), 7.701 (s, 1H). MS (FAB) m/z 265 (M+H)$^+$, 287 (M+Na)$^+$.

B

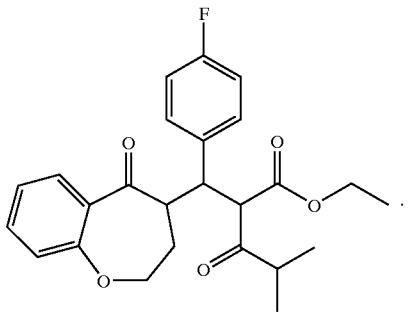

An oven-dried 250-mL 3-neck flask purged with argon was charged with anhydrous THF (30 mL) and lithium bis(trimethylsilyl)amide (1M in THF, 57.9 mL, 0.058 mol, 1.8 equiv), then cooled to –78° C. in a dry ice-acetone bath. A solution of Example 1 Part A compound (7.824 g, 0.0482 mol, 1.5 equiv) in dry THF (6 mL) was added via cannula and the enolate allowed to generate over 1 hr at –78° C. Then a solution of Part A compound (8.50 g, 0.0322 mol, 1 equiv) in dry THF (6 mL) was added via cannula and the resulting amber solution stirred at −78° C. for 30 min, then at 0° C. for 30 min. The reaction was quenched with glacial acetic acid (6 mL), then poured into satd aq NH₄Cl. The mixture was extracted with Et₂O (100 mL) and the ethereal extract was washed with H₂O (2×30 mL) and satd aq NaCl. The organic was dried over anhydrous Na₂SO₄, vacuum filtered and concentrated by rotary evaporation in vacuo to a yellow oil (17.19 g): MS (FAB) m/z 427 (M+H)⁺.

C

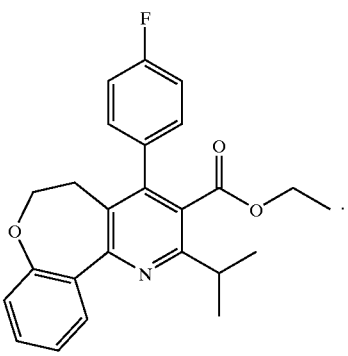

The crude Part B compound (17.19 g), NH₄OAc (11.0 g, 0.142 mol, 4.4 equiv), and Cu(OAc)₂ monohydrate (24.2 g, 0.119 mol, 3.7 equiv) were dissolved in glacial HOAc (120 mL) under argon and heated at gentle reflux for 20 hrs. The reaction was cooled to rt, then poured into an ice cold solution of conc NH₄OH (100 mL) in H₂O (200 mL). The mixture was extracted with Et₂O (200 mL+2×100 mL), then the combined ethereal extracts was washed with H₂O (2×100 mL) and satd aq NaCl. The extract was dried over anhydrous Na₂SO₄, vacuum filtered and concentrated by rotary evaporation in vacuo. The resulting brown oil was chased with hexanes to remove HOAc, followed by drying in vacuo. Purification in two batches on two SiO₂ flash columns (5 cm×22 cm) with 5% EtOAc/Hexanes afforded the product as a yellow oil which crystallized upon sitting (5.98 g, 0.0148 mol, 46% for two steps):

¹H NMR (CDCl₃) δ 0.959 (t, J=7 Hz, 3H), 1.164 and 1.359 (d's, J=7 Hz, 6H, 1:4 ratio), 2.557 (t, J=6.2 Hz, 2H), 2.897 and 3.146 (m's, J=7 Hz, 1H, 1:4 ratio), 4.006 (q, J=7 Hz, 2H), 4.418 (t, J=6.2 Hz, 2H), 6.710–7.578 (m, 7H), 7.898 (d, J=7.5 Hz, 1H); MS (ESI+Q) m/z 406 (M+H)⁺.

D

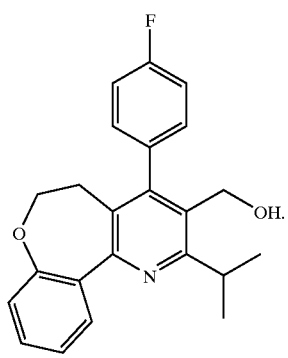

Part C compound (5.78 g, 0.0143 mol, 1 equiv) was dissolved in dry THF (70 mL) under argon and cooled to 0° C. A solution of LiAlH₄ in THF (1M, 28.5 mL, 0.0285 mol, 2 equiv) was added slowly. The reaction was stirred at rt for 2 hrs, followed by 25 min at reflux. TLC (SiO₂, 5% EtOAc/CH₂Cl₂, Rf=0.24). The reaction was cooled to 0° C., then carefully quenched with H₂O (2.3 mL), 15% aq NaOH (2.3 mL), and H₂O (4.7 mL). The white mixture was stirred at rt for 10 min, then vacuum filtered and the solid washed with EtOAc. The filtrate was concentrated by rotary evaporation in vacuo to a yellow oil. Purification on a SiO₂ flash column (5 cm×20 cm) with a gradient of 4% to 8% EtOAc/CH₂Cl₂ afforded the product as a white solid (4.082 g, 0.0112 mol, 79%):

¹H NMR (CDCl₃) δ 1.402 (d, J=6.6 Hz, 6H), 2.463 (t, J=6.2 Hz, 2H), 3.532 (m, J=6.6 Hz, 1H), 4.382 (t, J=6.2 Hz, 2H), 4.461 (d, J=5.3 Hz, 2H), 7.097 (d, J=7.9 Hz, 1H), 7.168 (t, J=8.8 Hz, 2H), 7.233–7.397 (m, 4H), 7.929 (d, J=7.5 Hz, 1H); MS (ESI+Q) m/z 364 (M+H)⁺.

E

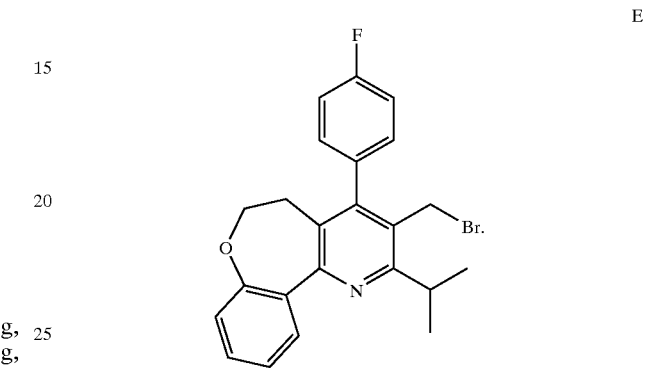

The Part D alcohol (3.066 g, 8.437 mmol, 1 equiv), dissolved in dry CH₂Cl₂ (60 mL) under argon at 0° C., was treated by dropwise addition of a 1M solution of PBr₃ in CH₂Cl₂ (16.9 mL, 16.9 mmol, 2 equiv). The reaction was stirred at rt for 30 min, at which time the reaction was recooled to 0° C. and treated with satd aq NaHCO₃ (90 mL). The mixture was diluted with CH₂Cl₂ (50 mL), the layers were separated, and the organic washed with H₂O (2×50 mL) and satd aq NaCl (50 mL). The organic was dried over anhydrous Na₂SO₄, filtered and concentrated in vacuo. TLC (SiO₂, 5% EtOAc/CH₂Cl₂, Rf=0.69). The residue was purified by SiO₂ flash chromatography (3.8 cm×15 cm column) with CH₂Cl₂ to obtain product as white solid (2.97 g, 6.97 mmol, 83%):

¹H NMR (CDCl₃) δ 1.403 (d, J=6.6 Hz, 6H), 2.430 (t, J=6.2 Hz, 2H), 3.459 (m, J=6.6 Hz, 1H), 4.290 (s, 2H), 4.356 (t, J=6.2 Hz, 2H), 7.087 (d, J=7.9 Hz, 1H), 7.183 (t, J=7.5 Hz, 2H), 7.263–7.397 (m, 4H), 7.910 (d, J=7.5 Hz, 1H); MS (ESI+Q) m/z 426/428 (M+H)⁺.

F

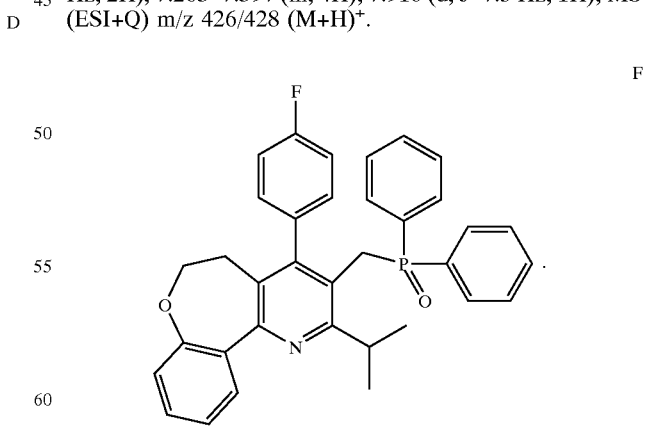

The Part E bromide (2.97 g, 6.967 mmol, 1 equiv) and ethyl diphenylphosphinite (1.7 mL, 7.663 mmol, 1.1 equiv) were heated at reflux under argon for 1.5 hrs. TLC (SiO₂, 30% EtOAc/CH₂Cl₂, product Rf=0.47). The reaction was cooled in an ice bath, then the solid collected by vacuum filtration in Buchner funnel; the solid was washed with small volumes of toluene, followed by hexanes. This afforded product as white solid (3.48 g, 6.35 mmol, 91%):

$^1$H NMR (CDCl$_3$) δ 1.256 (d, J=6.6 Hz, 6H), 2.334 (t, J=6 Hz, 2H), 3.33 (m, 1H), 3.716 (d, J=13.6 Hz, 2H), 4.252 (t, J=6 Hz, 2H), 6.767 (br t, J=5.3 Hz, 2H), 6.895 (t, J=8.5 Hz, 2H), 7.072 (d, J=7.9 Hz, 1H), 7.284 (t, J=7.4 Hz, 1H), 7.320–7.420 (m, 9H), 7.460–7.520 (m, 2H), 7.929 (d, J=7.4 Hz, 1H); MS (ESI+Q) m/z548 (M+H)$^+$.

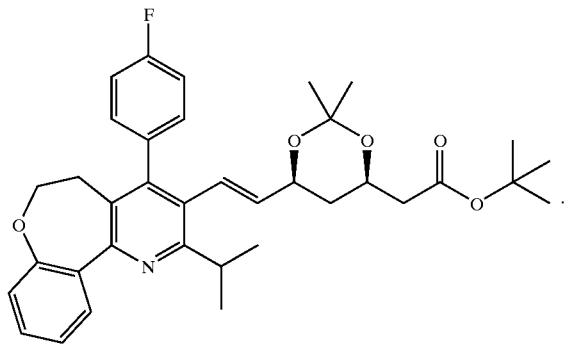

G

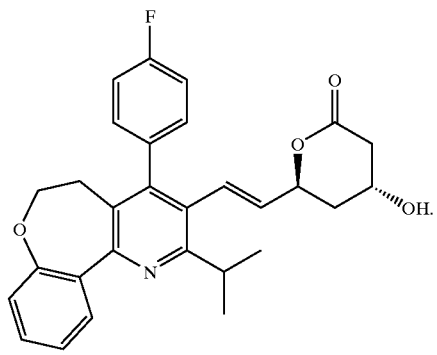

H

An oven-dried 50-mL flask charged with the Part F diphenylphosphine oxide (1.00 g, 1.826 mmol, 1 equiv) was chased with anhydrous toluene (3×5 mL), dried on hi-vacuum, and filled with argon. The dry solid was dissolved in dry THF (10 mL) and the resulting suspension cooled to 0° C. nBuLi solution (Aldrich, titrated with diphenylacetic acid: 2.4 M in hexanes; 0.80 mL, 1.92 mmol, 1.05 equiv) was added slowly dropwise over 20 min. The resulting dark amber-colored solution was allowed to stir at 0° C. for 1 hr. The Example 1 A(1) aldehyde (0.566 g, 2.192 mmol, 1.2 equiv) in an oven-dried 100-mL flask (material previously chased with anhydrous toluene (3×5 mL) and dried in vacuo) under argon atmosphere was dissolved in dry THF (5 mL) and cooled to −78° C. The anion solution was added via cannula to the aldehyde solution over a period of 25 min, then the dark green-colored solution was stirred at −78° C. for 1.5 hrs. The acetone/dry ice bath was then removed and the reaction allowed to slowly warm to room temperature; the initially green solution became an orange mixture. After 2 hrs, the reaction was quenched with half-satd aq NaCl (60 mL), extracted with Et$_2$O (100 mL), then washed the organic with H$_2$O and satd aq NaCl. Purification by SiO$_2$ flash chromatography (3.8 cm×15 cm column) afforded the product as a white foam (556 mg, 0.946 mmol, 52%). Also recovered unreacted diphenylphosphine oxide (445 mg, 0.8127 mmol):

$^1$H NMR (CDCl$_3$) δ 0.890 (q, 1H), 1.323–1.462 (m, 21H), 1.595 (d, 1H), 2.249 (dd, J=15.4 Hz, 6.2 Hz, 1H), 2.403 (dd, J=15.4 Hz, 7.0 Hz, 1H), 2.516 (t, J=6.2 Hz, 2H), 3.406 (m, 1H), 4.197–4.295 (m, 2H), 4.407 (m, 2H), 5.288 (dd, J=16.2 Hz, 5.7 Hz, 1H), 6.327 (dd, J=16.2 Hz, 1.3 Hz, 1H), 7.076–7.142 (m, 5H), 7.277–7.399 (m, 2H), 7.943 (d, J=7.5 Hz, 1H); MS (ESI+Q) m/z 588 (M+H)$^+$.

The Part G compound (0.230 g, 0.391 mmol) was dissolved in dry CH$_2$Cl$_2$ (5 mL) under an argon atmosphere and cooled to 0° C. Trifluoroacetic acid (0.5 mL) was added and the mixture was stirred at rt for 6 hrs. TLC (SiO$_2$, 20% EtOAc/CH$_2$Cl$_2$, Rf=0.31). The reaction solution was transferred to a separatory funnel and treated with satd aq NaHCO$_3$ (25 mL), extracted with EtOAc (100 mL), and the organic washed with satd aq NaHCO$_3$ and satd aq NaCl. The organic was dried over anhydrous Na$_2$SO$_4$, filtered and concentrated by rotary evaporation in vacuo. The residue was purified by SiO$_2$ flash chromatography (1.9 cm×15 cm column) to afford the product as a white solid (160 mg, 0.338 mmol, 86%):

$^1$H NMR (CDCl$_3$) δ 1.304 (d, J=6.6 Hz, 6H), 1.442–1.690 (m, 2H), 2.476–2.678 (m, 4H), 3.339 (m, 1H), 4.157 (m, 1H), 4.389 (t, J=6.2 Hz, 2H), 5.076 (m, 1H), 5.320 (dd, J=16.2 Hz, 10.1 Hz, 1H), 6.489 (d, J=16.2 Hz, 1H), 7.06–7.16 (m, 5H), 7.281 (t, 1H), 7.368 (t, 1H), 7.914 (d, J=7.5 Hz, 1H); MS (ESI+Q) m/z 474 (M+H)$^+$.

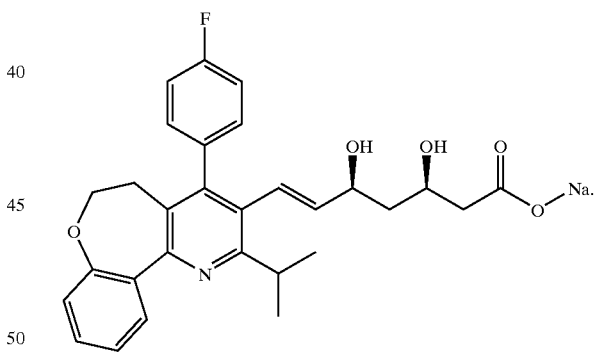

I

The Part H lactone (148 mg, 0.3125 mmol, 1 equiv) was dissolved in THF (3 mL), treated with 1N aq NaOH (0.391 mL, 0.3907 mmol, 1.25 equiv), and stirred at rt. TLC (SiO$_2$, 0.5:0.5:9 HOAc/MeOH/CH$_2$Cl$_2$, Rf=0.25). After 30 min, the solvents were removed by rotary evaporation in vacuo and the residue dried on hi-vacuum. A SP207 Na-form resin column (1.9 cm×10 cm bed) was prepared as follows: the resin was poured into a glass chromatography column equipped with fritted disc support, the resin was washed with satd aq NaHCO$_3$ (15 mL), satd aq NaCl (15 mL), and DI H$_2$O (100 mL, Milli-Q). The residue was taken up in Milli-Q DI H$_2$O (5 mL), applied to column, and eluted with Milli-Q DI H$_2$O (100 mL), 10% AcCN/H$_2$O (60 mL), and 25% AcCN/H$_2$O (125 mL). Product-containing fractions were combined and concentrated by rotary evaporation in vacuo to a small volume, then transferred to a 40-mL lyophilization jar, using additional H₂O to rinse out flask. The contents of the jar were frozen in an acetone-dry ice bath and lyophilized to afford the product as a white lyophilate (148 mg, 0.288 mmol, 92%):

¹H NMR (DMSO-d₆) δ 0.90–1.00 (m, 1H), 1.20–1.35 (m, 7H), 1.727 (dd, J=14.9 Hz, 7.9 Hz, 1H), 1.955 (dd, J=14.9 Hz, 4 Hz, 1H), 2.399 (t, J=6.2 Hz, 2H), 3.424–3.490 (m, 2H), 4.00–4.10 (m, 1H), 4.386 (t, J=6.2 Hz, 2H), 4.954 (br s, 1H), 5.354 (dd, J=16.2 Hz, 5.3 Hz, 1H), 6.297 (d, J=16.2 Hz, 1H), 7.12 (d, J=7.9 Hz, 1H), 7.20–7.46 (m, 7H), 7.802 (dd, J=7.9 Hz, 1.8 Hz, 1H); MS (ESI+Q) m/z 492 (M+H)⁺;

Anal. Calcd for C₂₉H₂₉FNO₅Na.H₂O: C, 65.53; H, 5.88; N, 2.64.

Found: C, 65.46; H, 5.70; N, 2.52.

EXAMPLE 3

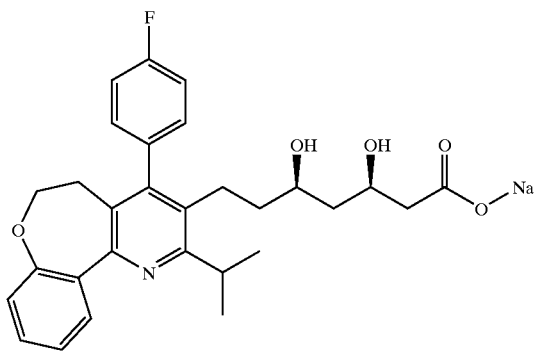

A.

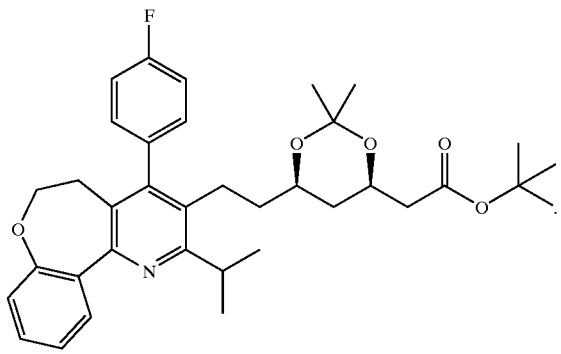

The Example 2 Part G compound (200 mg, 0.3403 mmol, 1 equiv) was hydrogenated at 45 psi H₂ in anhydrous MeOH (30 mL) with 10% Pd-C (40 mg, 20 wt %) for 2 hrs. The catalyst was washed with small portions of MeOH and the filtrate was concentrated by rotary evaporation in vacuo. The residue was purified by SiO₂ flash chromatography (2.5 cm×13 cm) with 3% EtOAc/CH₂Cl₂ to afford the product as a white foam (193 mg, 0.3273 mmol, 96%): HPLC (Shimadzu YMC S-5 C18 4.6×50 mm column, 4 min gradient @ 4 mL/min, UV detection 220 nM; start % B=60, final % B=100; A=10:90 MeOH/H₂O+0.2% H₃PO₄) R.T.= 4.35 min (100%);

¹H NMR (CDCl₃) δ 0.902 (q, J=12.3 Hz, 1H), 1.27–1.60 (m, 24 H), 2.212 (dd, J=15.4 Hz, 6.2 Hz, 1 H), 2.25–2.42 (m, 4 H), 2.50–2.60 (m, 1 H), 3.336 (m, 1 H), 3.599 (m, 1 H), 4.10–4.20 (m, 1 H), 4.328 (t, J=6.2 Hz, 2 H), 7.067 (d, J=7.9 Hz, 1 H), 7.1416 (d, J=6.6 Hz, 4 H), 7.265 (t, J=7.5 Hz, 1 H), 7.340 (t, J=7.5 Hz, 1 H), 7.901 (d, J=7.5 Hz, 1 H); MS (ESI+Q) m/z 590 (M+H)⁺.

B.

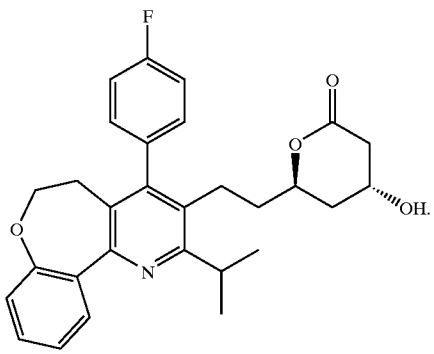

Part A compound (258 mg, 0.4375 mmol) was dissolved in dry CH₂Cl₂ (5 mL) under argon, cooled to 0° C. and treated with trifluoroacetic acid (0.5 mL). Stirring was continued at room temperature for 7 hrs, at which time the reaction was complete by HPLC. Saturated aqueous NaHCO₃ (25 mL) was added to the reaction, the reaction was diluted with EtOAc (100 mL), and the layers separated. The organic was washed with saturated aqueous NaHCO₃ and saturated aqueous NaCl, then dried over anhydrous Na₂SO₄, filtered and concentrated in vacuo. Purification by SiO₂ flash chromatography (1.9 cm×15 cm) with 20% EtOAc/CH₂Cl₂ afforded a white foam (163 mg, 0.343 mmol, 78%): HPLC (Shimadzu, YMC S-5 C18 4.6×50 mm column, 4 min gradient @ 4 mL/min, UV detection 220 nM; start % B=0, final % B=100; A=10:90 MeOH/H₂O+0.2% H₃PO₄, B=90:10 MeOH/H₂O+0.2% H₃PO₄) R.T.=3.81 min (94.6%);

¹H NMR (CDCl₃) δ 1.37 (d, J=6.6 Hz, 6 H), 1.45–1.85 (m, 4 H), 2.40–2.75 (m, 6 H), 3.327 (m, 1 H), 4.285 (br s, 1 H), 4.350 (t, J=6.2 Hz, 2 H), 4.49 (m, 1 H), 7.093 (d, J=7.9 Hz, 1 H), 7.181 (d, J=7.0 Hz, 4 H), 7.291 (t, J=7.5 Hz, 1 H), 7.3697 (t, J=7.5 Hz, 1 H), 7.912 (d, J=7.5 Hz, 1 H); MS (ESI+Q) m/z 476 (M+H)⁺.

C.

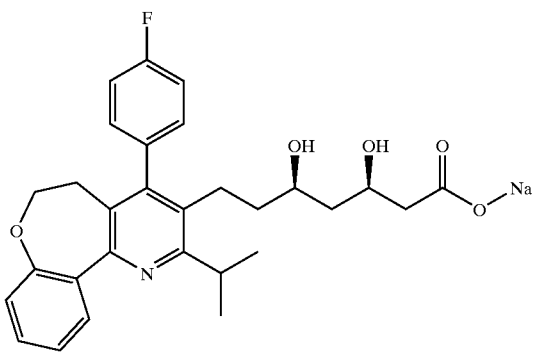

Part B compound (149 mg, 0.3133 mmol, 1 equiv) was dissolved in THF (3 mL) and 1N aqueous NaOH (0.392 mL, 0.3916 mmol, 1.25 equiv) and stirred at room temperature for 30 min. The solvent was removed by rotary evaporation in vacuo and the residue was dried under high-vacuum. An SP207 resin column (1.9 cm×10 cm) was prepared as follows: resin was poured into a glass chromatography column equipped with fritted disc support and the resin was washed sequentially with saturated aqueous NaHCO$_3$ (15 mL), saturated aqueous NaCl (15 mL), and Milli-Q H$_2$O (100 mL). The dried residue was taken up in Milli-Q H$_2$O (8 mL) and carefully applied to top of the column. The column was eluted with Milli-Q H$_2$O (100 mL), 10% AcCN/H$_2$O (60 mL), 20% AcCN/H$_2$O (60 mL), and 25% AcCN/H$_2$O (100 mL). Product-containing fractions were combined and concentrated by rotary evaporation to a small volume, and transferred to a 40-mL lyophilization jar. The contents were frozen in acetone-dry ice bath and lyophilized. This afforded the product as a white lyophilate (149 mg, 0.289 mmol, 92%): HPLC (Shimadzu, YMC S-5 C18 4.6×50 mm column, 4 min gradient @ 4 mL/min, UV detection 220 nM: start % B=0, final % B=100; A=10:90 MeOH/H$_2$O+0.2% H$_3$PO$_{41}$ B=10:90 MeOH/H$_2$O+0.2% H$_3$PO$_4$) R.T.=3.58 min (92.9%);

$^1$H NMR (DMSO-d$_6$) δ 1.048–1.105 (m, 1 H), 1.232–1.50 (m, 9 H), 1.750 (dd, J=14.9 Hz, 8.3 Hz, 1 H), 1.966 (dd, J=14.9 Hz, 4.0 Hz, 1 H), 2.298–2.356 (m, 3 H), 3.335–3.424 (m, 2 H), 3.616–3.656 (m, 1 H), 4.3166 (t, J=6.2 Hz, 2 H), 4.711 (br s, 1 H), 7.098 (d, J=7.9 Hz, 1 H), 7.276–7.43 (m, 6 H), 7.773 (d, J=7.5 Hz, 1 H); MS (ESI+Q) m/z 494 (M+H)$^+$ for acid form.

The following Examples may be prepared employing procedures set out herein and in the working Examples.

EXAMPLES 4 TO 26

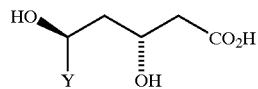

where Y is as set out below

EXAMPLE 4

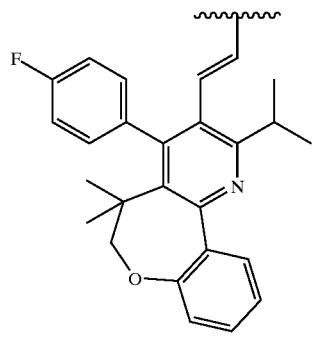

EXAMPLE 5

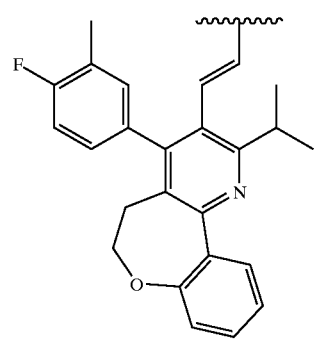

EXAMPLE 6

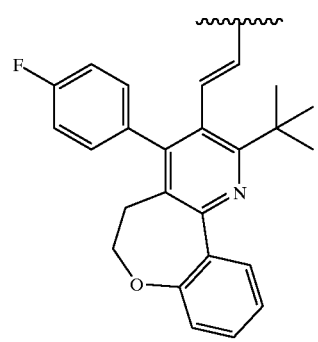

EXAMPLE 7

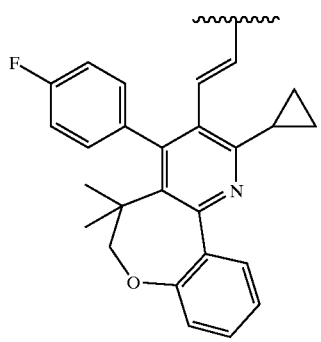

EXAMPLE 8

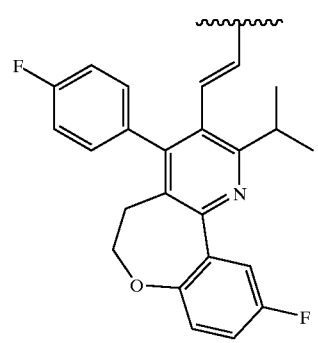

EXAMPLE 9
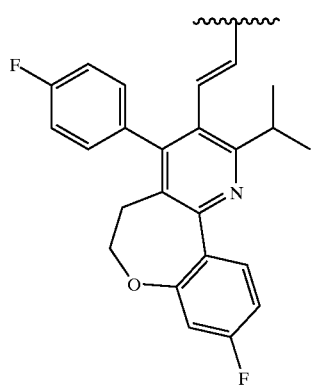
EXAMPLE 10
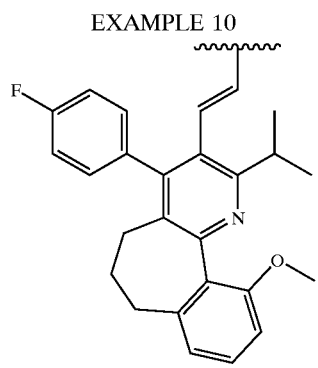
EXAMPLE 11
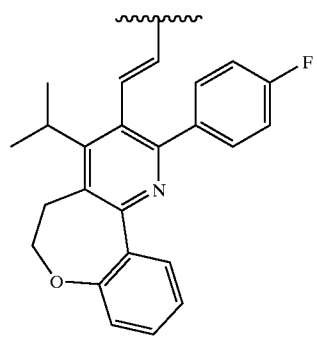
EXAMPLE 12
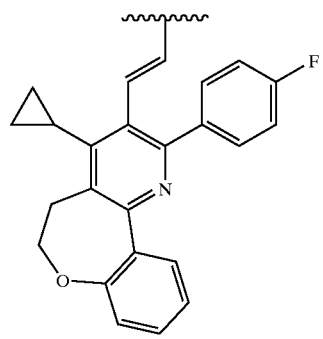
EXAMPLE 13
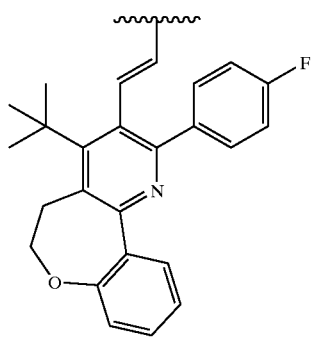
EXAMPLE 14
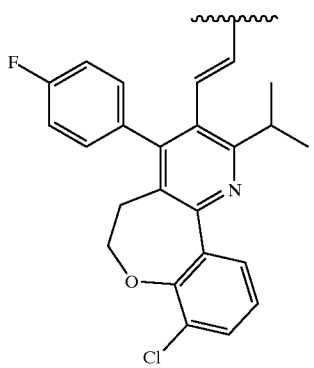
EXAMPLE 15
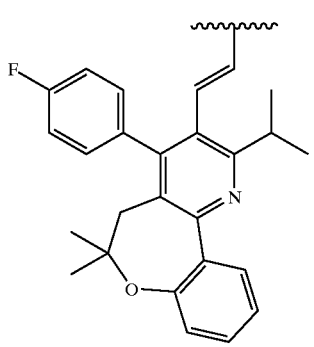
EXAMPLE 16
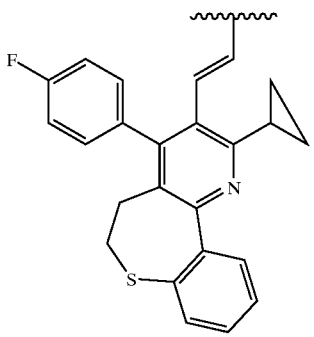

EXAMPLE 17
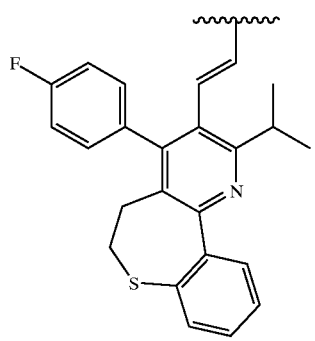
EXAMPLE 18
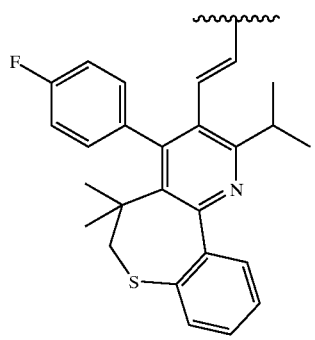
EXAMPLE 19
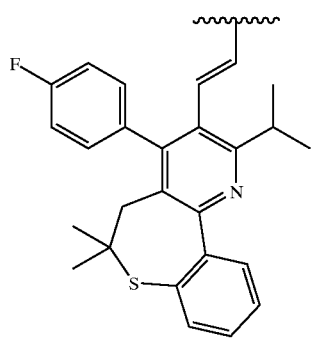
EXAMPLE 20
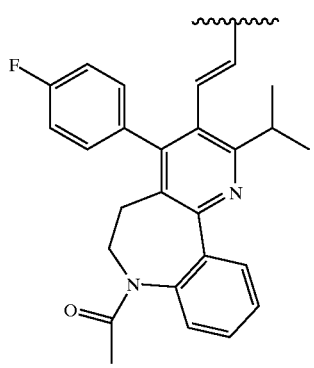
EXAMPLE 21
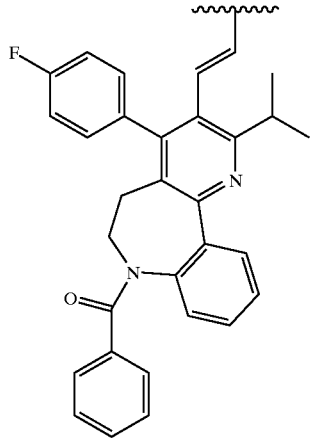
EXAMPLE 22
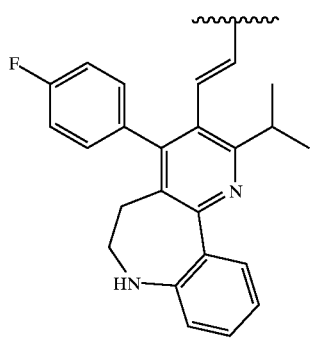
EXAMPLE 23
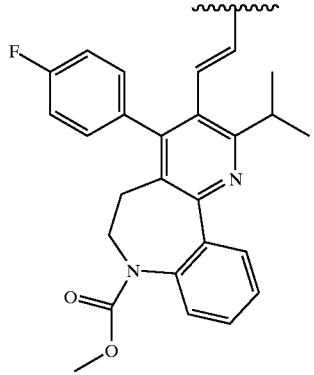

EXAMPLE 24

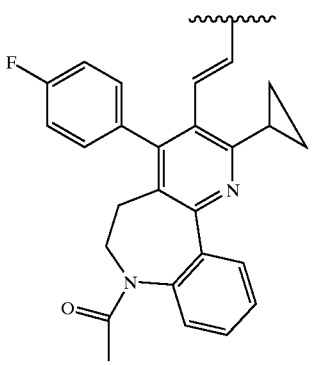

EXAMPLE 25

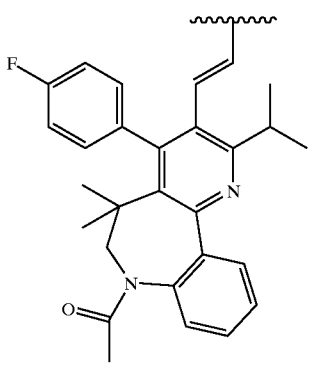

EXAMPLE 26

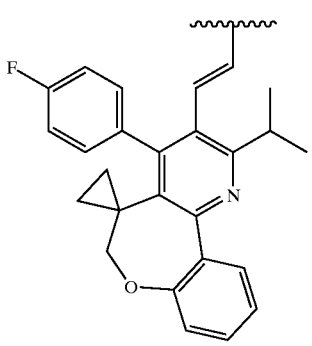

EXAMPLE 27
Preparation of Pyridine Aldehyde (18) (Scheme 5)

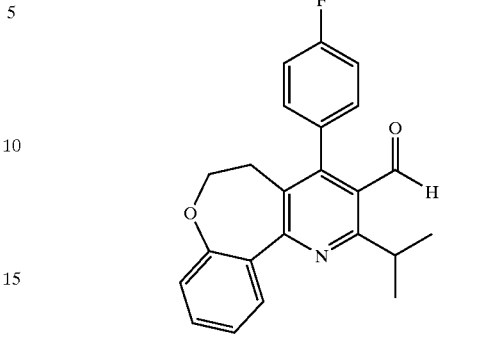
(18)

Following the procedure outlined in reaction Scheme and the description thereof, the Example 27 aldehyde is obtained.

An example of a typical preparation of the aldehyde is set out below.

To a 500 mL round bottom flask equipped with a magnetic stirrer and a nitrogen inlet was charged compound (17) (Scheme 5)

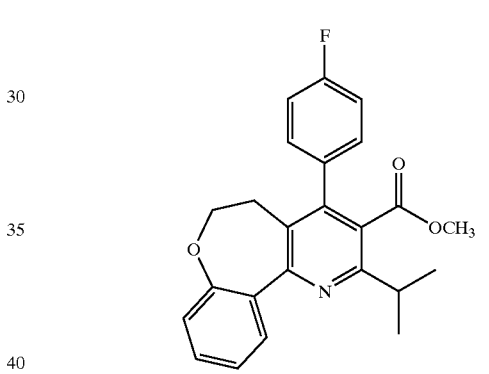
(17)

(50 g, 128.4 mmol) (prepared as described in Example 2 Parts A, B and C except methyl isobutyryl acetate is substituted for ethyl isobutyryl acetate) and toluene (170 mL). The mixture is stirred at 20–25° C. until a clear solution is obtained. A solutin of 65% Red-Al in toluene (57.8 mL, 192.6 mmol) is added and the reaction mixture is heated to 80° C. until complete as determined by HPLC. The reaction mixture is cooled to 20° C. and quenched by pouring it into cold (0–5° C.) 20% HCl (495 mL). Phases are separated and the spent toluene phase is discarded. The pH of the aqueous phase is adjusted from <0 to 4–5 with 10N NaOH. Ethyl acetate (500 mL) is added and the pH adjustment continued to 7–8. The phases are separated. The aqueous phase is extracted with additional ethyl acetate (2×500 mL). The combined rich ethyl acetate solution is washed with water (3×250 mL) and concentrated under reduced pressure to ~465 mL. This solution is carried through to the next oxidation step.

The rich ethyl acetate solution is charged from above into a three neck 1-L flask equipped with mechanical stirring, temperature controller, and addition funnel and cooled to 0–5° C. To the slurry, potassium bromide (1.53 g, 12.8 mmol) and TEMPO (2,2,6,6-tetramethyl-1-piperidinyloxy) (0.20 g, 1.28 mmol) are added. The pH of NaOCl (sodium hypochlorite) solution (212.1 mL) is adjusted to ~9.1 and added to the slurry at a rate such that the temperature remained at 0–5° C. Stirring is continued at 0–5° C. until the reaction is complete as determined by HPLC. The aqueous phase is extracted with EtOAc (2×200 mL). The combined rich organic phase is washed with a 1:1 solution of sat. aq. Na$_2$S$_2$O$_3$ (sodium thiosulfate) (75 mL) and water (75 mL) followed by wash of the rich organic phase with 1N NaOH (250 mL). The rich organic phase is washed with water (250 mL) and concentrated to ~100 mL under reduced pressure. Isopropanol (IPA) (400 mL) is added and the resulting mixture is heated to reflux (80–85° C.). The solution is distilled to a volume of ~250 mL. Water (50 mL) is added and the crystal slurry is stirred at 70–80° C. for 1 h then allowed to cool to 20–25° C. over at least 1 h. The slurry is held at 20–25° C. for at least 1 h before collecting the solid by filtration on a Buchner funnel. The cake is washed with cold (0° C.) IPA/water (4:1) (2×50 mL) and dried to a constant weight under vacuum at 40° C. to afford title aldehyde.

EXAMPLE 28

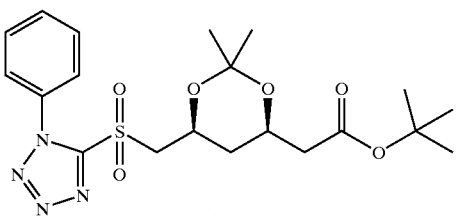

(16) (Scheme 5)

A. Preparation of Sulfone (15)

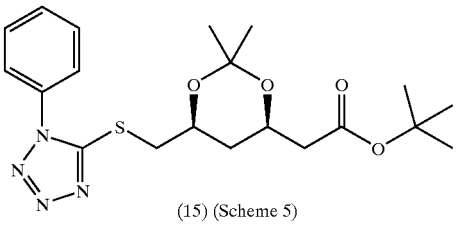

(15) (Scheme 5)

To a 250 mL flask was charged Kaneka alcohol (12) (Scheme 6) (10.0 g, 38.41 mmol), methylene chloride (100 mL), and triethylamine (11.75 mL, 84.51 mmol) and cooled to −30° C. Triflic anhydride (7.11 mL, 42.25 mmol) was added via a syringe at a rate to maintain the temperature at −35 to −25° C., ~15 min. The reaction mixture was stirred at −30° C. for ~30 min and checked for disappearance of Kaneka alcohol by TLC. A slurry of 1-phenyl-1H-tetrazole-5-thiol (7.19 g, 40.34 mmol) in methylene chloride (50 mL) was added to the triflate solution. After the reaction was complete, water (100 mL) was added and the mixture was stirred for ~5 min. The phases were separated and the aqueous phase was discarded. The rich orgnaic phase was washed with water (100 mL) for ~5 min and phases separated. The rich organic phase was washed with saturated NaHCO$_3$ (100 mL) for ~15 min and phases separated. The rich organic phase was concentrated to ~50 mL. The solution was taken to the next step for further transformation.

B. Preparation of Sulfone (16)

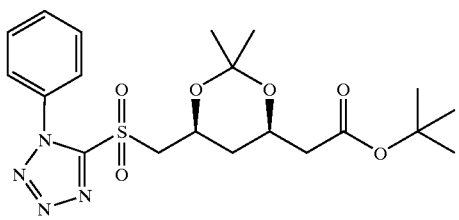

IPA (150 mL) was added to the Part A sulfide solution from the above step. The solution was cooled to 0–5° C. To the stirred solution of sulfide, a solution of (NH$_4$)$_6$MO$_7$O$_{24}$.4H$_2$O (ammonium heptamolybdate tetrahydrate) (4.75 g, 3.84 mmol) in 30% H$_2$O$_2$ (hydrogen peroxide) was added dropwise during ~15 min, maintaining the temperature of the solutin at 0–5° C. The conversion of sulfide to sulfone was monitored by HPLC ~24 h. After completion of the reaction, methylene chloride was distilled out. The pot temperature was maintained at not more than 25° C. The crystal slurry was distilled to a volume of 230 mL with IPA and the resulting slurry was stirred for at least 1 h at 20–22° C. The solid was collected by vacuum filtration, the cake washed with IPA/water (4:1, 25 mL) followed by drying under vacuum at 40° C. to constant weight affording 12.8 g (74%) of the title sulfone as a white crystalline solid.

EXAMPLE 29

Preparation of Olefin (19)

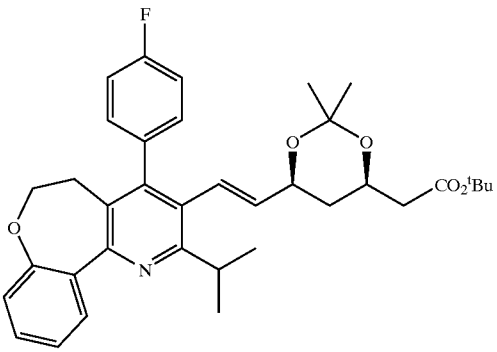

Following the procedure set out in reaction Scheme 5 and the description thereof, the Example 27 pyridine derivative and the Example 28 sulfone are employed to prepare the title compound.

An example of a typical preparation of the Example 29 compound is set out below.

An N$_2$ purged 250 mL 3-neck rb flask is charged with Example 27 pyridine derivative (18) (5 g, 13.9 mmol), Example 28 sulfone (16) (6.9 g, 15.3 mmol) and THF (75 mL). The stirred solution is cooled to −74 to −78° C. Slowly a 1M solution of LiHMDS (lithium bis(trimethylsilyl) amide) (15.3 mL, 15.3 mmol) in THF is charged at a rate such that the temperture remained between −70 and −78° C. After addition of the base is complete, the reaciton mixture is warmed to ~−45° C. over ~15 minutes. The stirred reaction is quenched at −70° C. by slow addition of sat. aq. NH$_4$Cl (7.5 mL) solution and water (38 mL). The dry ice bath is removed and the solution is warmed to 20–25° C. from the reaction mixture. Ethyl acetate (50 mL) is added, the mixture agitated, and layers separated. The organic layer is washed with saturated sodium bicarbonate solution (2×38 mL) followed by brine (25 mL) and concentrated to a volume of 50 mL. Acetonitrile (50 mL) is added and the solution is concentrated to a volume of 50 mL. This step is repeated. Water (~5–6 mL) is slowly added to the hot solution (60–70° C.) until the cloud point is reached. The thin slurry is held for 30 min at high temperature and then slowly cooled over several hours with stirring. The product is filtered, cake is washed with a 5:1 mixture of acetonitrile and water, and dried to afford the title compound.

EXAMPLE 30

Preparation of the Final Compound

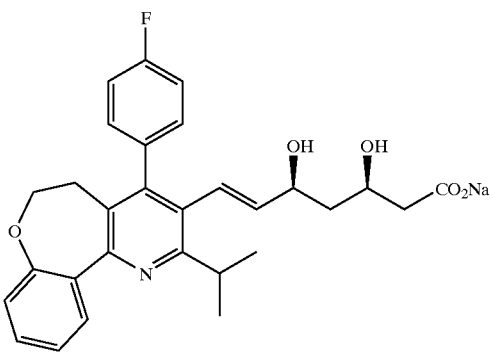

Following the procedure of Example 3 Parts B and C, the Example 29 compound is employed to prepare the title compound in the form of the sodium salt.

What is claimed is:

1. A compound having the structure

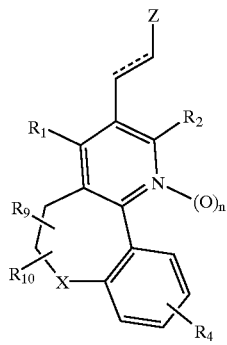

wherein
X is O, S, SO, $SO_2$ or $NR_7$;
Z is

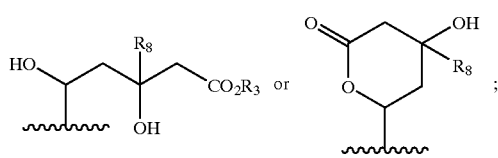

also referred to as the δ-lactone;
n is 0 or 1;
$R_1$ and $R_2$ are the same or different and are independently selected from alkyl, arylalkyl, cycloalkyl, alkenyl, cycloalkenyl, aryl, heteroaryl or cycloheteroalkyl;
$R_3$ is H or lower alkyl or a metal ion
$R_4$ is H, halogen, $CF_3$, hydroxy, alkyl, alkoxy, carboxyl, carboxyalkyl-, aminoalkyl, amino, alkanoylamino, aroylamino, cyano, alkoxyCON($R_{7d}$)-, $R_{7f}R_{7g}NCO_2$—, $R_{7f}R_{7g}NCO$—, $R_{7e}SO_2N(R_{7d})$-, $R_{7f}R_{7g}NSO_2N(R_{7d})$-, $R_{7e}OCO_2$ or $R_{7e}OCO$;

$R_7$ is H, alkyl, aryl, alkanoyl, aroyl or alkoxycarbonyl, $R_{7a}SO_2$—, $R_{7b}R_{7c}NSO_2$— or $R_{7b}R_{7c}NCO$—;

$R_{7a}$ and $R_{7e}$ are the same or different and are independently selected from alkyl, arylalkyl, cycloalkyl, alkenyl, cycloalkenyl, aryl, heteroaryl or cycloheteroalkyl;

$R_{7b}$ and $R_{7c}$, and $R_{7f}$ and $R_{7g}$, and $R_{7d}$ are the same or different and are independently selected from H, alkyl, arylalkyl, cycloalkyl, alkenyl, cycloalkenyl, aryl, heteroaryl or cycloheteroalkyl;

$R_8$ is H or lower alkyl;

$R_9$ and $R_{10}$ are the same or different and are independently selected from H or alkyl; or where at least one of $R_9$ and $R_{10}$ is alkyl, $R_9$ and $R_{10}$ may be taken together with the carbon to which they are attached to form a 3 to 7 membered spirocyclic ring;

and ⟋ represents a single bond or a double bond (which may be cis or trans);

or a pharmaceutically acceptable salt thereof (where $R_3$ is H), or an ester thereof, or a stereoisomer thereof.

2. The compound as defined in claim 1 wherein ⟋ is a double bond which is trans.

3. The compound as defined in claim 1 wherein Z is in the form of a pharmaceutically acceptable basic salt.

4. The compound as defined in claim 1 in the form of a pharmaceutically acceptable acid addition salt.

5. The compound as defined in claim 1 wherein Z is in the form of the δ-lactone.

6. The compound as defined in claim 1 wherein X is O, $SO_2$ or $NR_7$ where $R_7$ is $R_{7a}SO_2$—.

7. The compound as defined in claim 1 wherein $R_1$ and $R_2$ are independently selected from alkyl, cycloalkyl and aryl;
$R_4$ is H or halogen;
n is 0;
and X is O.

8. The compound as defined in claim 1 wherein $R_1$ is aryl, $R_2$ is alkyl or cycloalkyl;
$R_4$ is H;
n is 0;
X is O; and
⟋ is a trans double bond, in the form of a free acid or an alkali or alkaline earth metal salt or an amino acid salt.

9. The compound as defined in claim 8 wherein $R_1$ is phenyl which contains 1 or 2 substituents,
$R_2$ is alkyl or cycloalkyl;
$R_4$ is H;
X is O; and
⟋ is a trans double bond, in the form of a free acid or an alkali or alkaline earth metal salt or an amino acid salt.

10. The compound as defined in claim 9 wherein $R_1$ is 4-fluorophenyl, 4-fluoro-3-methylphenyl, or 3,5-dimethylphenyl; and
$R_2$ is isopropyl, t-butyl or cyclopropyl.

11. The compound as defined in claim 1 wherein Z has the structure

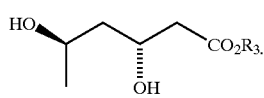

12. The compound as defined in claim 1 wherein X is SO, $SO_2$ or $NR_7$.

13. The compound as defined in claim 12 wherein $R_7$ is $R_{7a}SO_2—$, $R_{7b}R_{7c}NSO_2—$, or $R_{7b}R_{7c}NCO—$.

14. The compound as defined in claim 12 wherein $R_4$ is alkoxycarbonylamino-, $R_{7f}R_{7g}NCO_2—$, $R_{7e}SO_2N(R_{7d})—$ or $R_{7f}R_{7g}NSO_2N(R_{7d})—$.

15. A compound having the structure

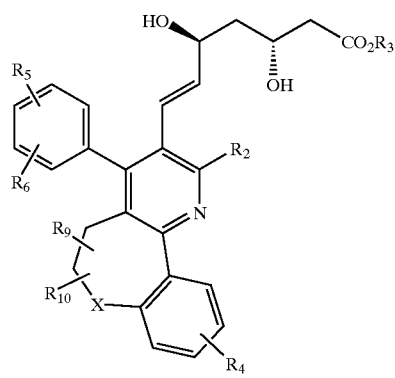

or an alkali or alkaline earth metal salt thereof or an amino acid salt or an acid addition salt via the pyridine, or the corresponding δ-lactone, wherein $R_5$ and $R_6$ are the same or different and are independently selected from H, halogen or alkyl and $R_2$ is alkyl or cycloalkyl;

$R_4$ is H;

$R_9$ and $R_{10}$ are each H;

X is O;

and $R_3$ is H.

16. The compound as defined in claim 15 wherein $R_5$ and $R_6$ are H and 4-fluoro;

H and 4-fluoro-3-methyl or 3,5-dimethyl; and $R_2$ is isopropyl, t-butyl or cyclopropyl.

17. The compound as defined in claim 15 having the structure

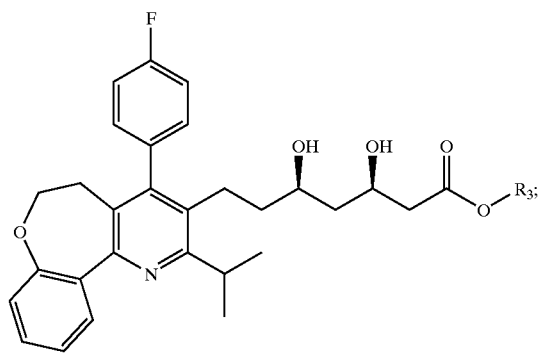

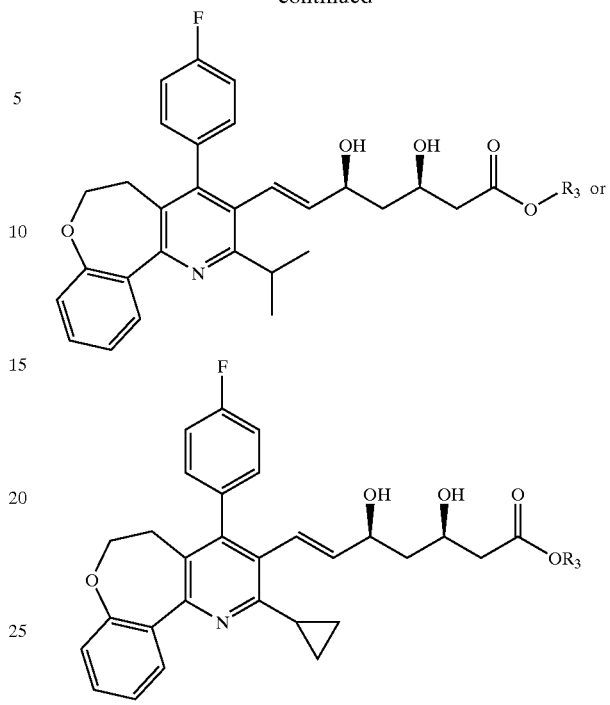

wherein $R_3$ is H; or an alkali or alkaline earth metal or an amino acid salt, or the δ-lactone thereof.

18. A compound of the structure

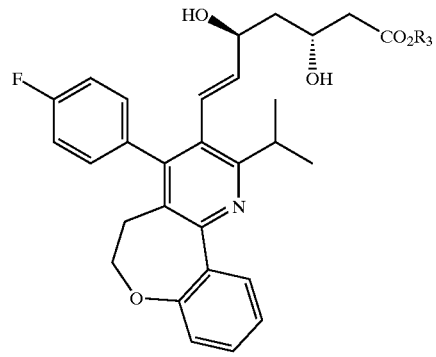

wherein $R_3$ is H; or an alkali or alkaline earth metal salt or an amino acid salt, or the δ-lactone thereof.

19. The compound as defined in claim 18 in the form of the sodium salt.

20. A pharmaceutical composition comprising a compound as defined in claim 1 and a pharmaceutically acceptable carrier therefor.

21. A method for treating hypercholesterolemia, dyslipidemia, hyperlipidemia, hyperlipoproteinemia, LDL Pattern B, LDL Pattern A, hypertriglyceridemia or atherosclerosis, or osteoporosis, which comprises administering to a mammalian species in need of such treatment a HMG-CoA reductase inhibiting effective amount of a compound as defined in claim 1.

22. A method of inhibiting cholesterol biosynthesis or lowering blood serum cholesterol levels, lowering LDL cholesterol and/or increasing HDL cholesterol, or treating dyslipidemia, mixed dyslipidemia, LDL Pattern B, LDL Pattern A, hyperlipidemia, hypercholesterolemia, hypo x-lipoproteinemia, hyperlipoproteinemia or hypertriglyceridemia, or reducing levels of Lp(a), or treating atherosclerosis, or treating osteoporosis and/or osteopenia, or reducing inflammatory markers, reducing C-reactive protein, or treating low grade vascular inflammation, stroke, dementia, or coronary heart disease, or preventing primary or secondary myocardial infarction, or treating stable or unstable angina, or preventing primary coronary events, or preventing secondary cardiovascular events, or treating peripheral vascular disease, treating peripheral arterial disease, or treating acute vascular syndromes, or reducing the risk of undergoing myocardial revascularization procedures, which comprises administering to a mammalian species in need thereof a HMG-CoA reductase inhibiting effective amount of a compound in accordance with claim 1.

23. A method for treating diabetes, Type 2 diabetes, insulin resistance, hyperglycemia, hyperinsulinemia, elevated blood levels of fatty acids or glycerol, obesity, LDL Pattern B, LDL Pattern A, Syndrome X, diabetic complications, or dysmetabolic syndrome, which comprises administering to a mammalian species in need of such treatment a HMG-CoA reductase inhibiting effective amount of a compound as defined in claim 1.

24. A method for treating drug-induced lipodystrophy, which comprises administering to a mammalian species in need of such treatment a HMG-CoA reductase inhibiting effective amount of a compound as defined in claim 1.

25. A compound having the structure

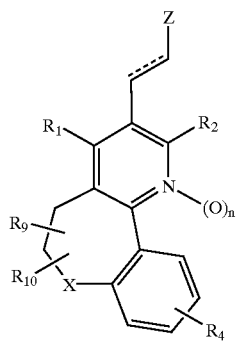

wherein X is O, S or $NR_7$;

Z is

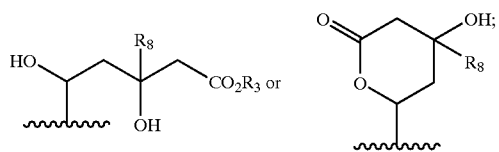

also referred to as the δ-lactone;

n is 0 or 1;

$R_1$ and $R_2$ are the same or different and are independently selected from alkyl, arylalkyl, cycloalkyl, alkenyl, cycloalkenyl, aryl, heteroaryl or cycloheteroalkyl;

$R_3$ is H or lower alkyl;

$R_4$ is H, halogen, $CF_3$, hydroxy, alkyl, alkoxy, alkanoylamino, aroylamino, or cyano;

$R_7$ is H, alkyl, aryl, alkanoyl, aroyl or alkoxycarbonyl;

$R_8$ is H or lower alkyl;

$R_9$ and $R_{10}$ are the same or different and are independently selected from H or alkyl;

and ⫽ represents a single bond or a double bond (which may be cis or trans);

or a pharmaceutically acceptable salt thereof (where $R_3$ is H), or an ester thereof, or a stereoisomer thereof.

* * * * *